(12) United States Patent
Keating et al.

(10) Patent No.: US 11,529,495 B2
(45) Date of Patent: Dec. 20, 2022

(54) EXPANDABLE MOUTH CATHETER

(71) Applicant: Neuravi Limited, Galway (IE)

(72) Inventors: Karl Keating, Galway (IE); Ronald Kelly, Galway (IE)

(73) Assignee: Neuravi Limited, Galway (IE)

( * ) Notice: Subject to any disclaimer, the term of this patent is extended or adjusted under 35 U.S.C. 154(b) by 48 days.

(21) Appl. No.: 17/017,276

(22) Filed: Sep. 10, 2020

(65) Prior Publication Data

US 2021/0069468 A1 Mar. 11, 2021

Related U.S. Application Data

(60) Provisional application No. 62/898,864, filed on Sep. 11, 2019.

(51) Int. Cl.
*A61M 25/00* (2006.01)
*A61M 25/01* (2006.01)
*A61M 25/06* (2006.01)

(52) U.S. Cl.
CPC .... *A61M 25/0074* (2013.01); *A61M 25/0052* (2013.01); *A61M 25/0147* (2013.01); *A61M 2025/0687* (2013.01); *A61M 2210/0625* (2013.01)

(58) Field of Classification Search
CPC .......... A61M 25/0074; A61M 25/0052; A61M 25/0147; A61M 2025/0687; A61M 2210/0625; A61M 2025/1052; A61M 2025/109; A61M 25/0102; A61M 25/0012; A61M 25/008; A61M 2025/0656; A61B 17/22; A61B 17/221; A61B 2017/22001; A61B 2017/22002; A61B 2017/22051; A61B 2017/22079; A61B 2017/2212; A61B 2017/22034; A61B 2017/22069; A61B 2017/2215; A61B 2017/22042
See application file for complete search history.

(56) References Cited

U.S. PATENT DOCUMENTS

| | | | |
|---|---|---|---|
| 4,243,040 A | 1/1981 | Beecher | |
| 4,324,262 A | 4/1982 | Hall | |
| 4,351,342 A | 9/1982 | Witta et al. | |
| 4,575,371 A | 3/1986 | Nordqvist et al. | |

(Continued)

FOREIGN PATENT DOCUMENTS

| CN | 1658920 A | 8/2005 |
|---|---|---|
| CN | 103071195 A | 5/2013 |

(Continued)

OTHER PUBLICATIONS

US 6,348,062 B1, 02/2002, Hopkins (withdrawn)

(Continued)

*Primary Examiner* — Bhisma Mehta
*Assistant Examiner* — Phoebe Anne Staton
(74) *Attorney, Agent, or Firm* — Troutman Pepper Hamilton Sanders LLP

(57) ABSTRACT

A catheter system that is actuatable to a deployed state and includes a catheter body and a dilator positioned at least partially within the lumen of the catheter. A distal end of the dilator can be releasably connected to a distal tip of the catheter body. The dilator can be retractable to expand and invert the distal tip and form a funnel shape in the deployed state.

18 Claims, 11 Drawing Sheets

(56) References Cited

U.S. PATENT DOCUMENTS

| | | |
|---|---|---|
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |

(56) References Cited

U.S. PATENT DOCUMENTS

| | | |
|---|---|---|
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 3,002,822 A1 | 8/2011 | Glocker et al. |
| 7,998,165 B2 | 8/2011 | Huffmaster |
| 3,021,379 A1 | 9/2011 | Thompson et al. |
| 3,021,380 A1 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |

(56) References Cited

U.S. PATENT DOCUMENTS

| | | |
|---|---|---|
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 2001/0001315 A1 | 5/2001 | Bates |
| 2001/0011182 A1* | 8/2001 | Dubrul ............. A61B 17/22 606/200 |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbul |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Safer et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |

(56) References Cited

U.S. PATENT DOCUMENTS

| | | |
|---|---|---|
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1* | 12/2007 | Okushi .......... A61B 17/320725 606/200 |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0030186 A1 | 2/2010 | Stivland |
| 2010/0030256 A1 | 2/2010 | Dubrul et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavaski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1* | 10/2013 | Baker ............... A61M 25/0053 156/244.11 |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eldenschink |
| 2014/0276922 A1 | 9/2014 | McLain et al. |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |

(56) References Cited

U.S. PATENT DOCUMENTS

| | | |
|---|---|---|
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0306311 A1* | 10/2015 | Pinchuk ............ A61M 5/16881 604/246 |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193591 A1 | 7/2018 | Jaroch et al. |
| 2018/0235743 A1 | 8/2018 | Farago et al. |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0255290 A1 | 8/2019 | Snyder et al. |
| 2019/0365411 A1 | 12/2019 | Avneri et al. |
| 2022/0125450 A1 | 4/2022 | Sirhan et al. |

FOREIGN PATENT DOCUMENTS

| | | |
|---|---|---|
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |

(56) References Cited

FOREIGN PATENT DOCUMENTS

| | | |
|---|---|---|
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| GB | 2498349 A | 7/2013 |
| GN | 1972728 A | 5/2007 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |

OTHER PUBLICATIONS

Extended European Search Report issued in corresponding European Patent Application No. 20 19 5533 dated Feb. 8, 2021.

Struffert, T., et al. "Intravenous flat detector CT angiography for non-invasive visualisation of intracranial flow diverter: technical feasibility" Eur Radiol 21:1797-1801 (2011).

* cited by examiner

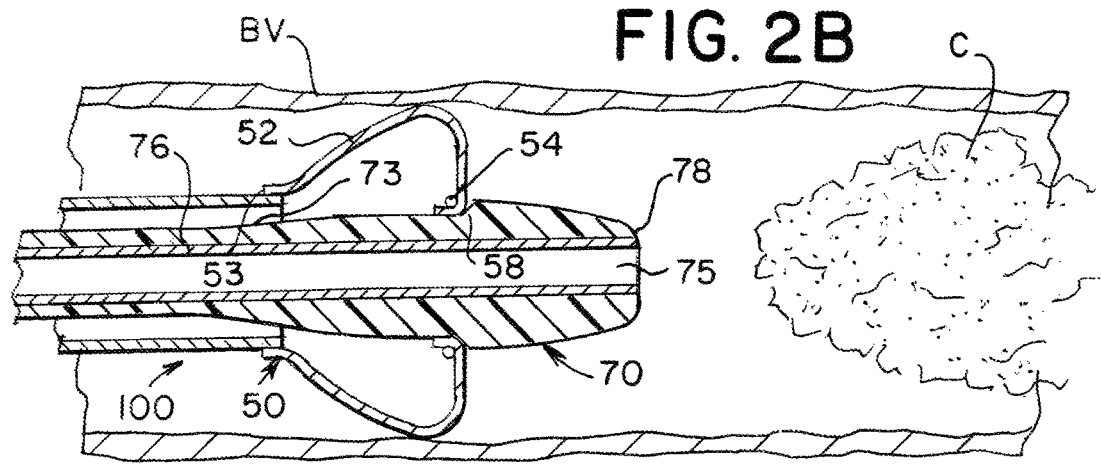
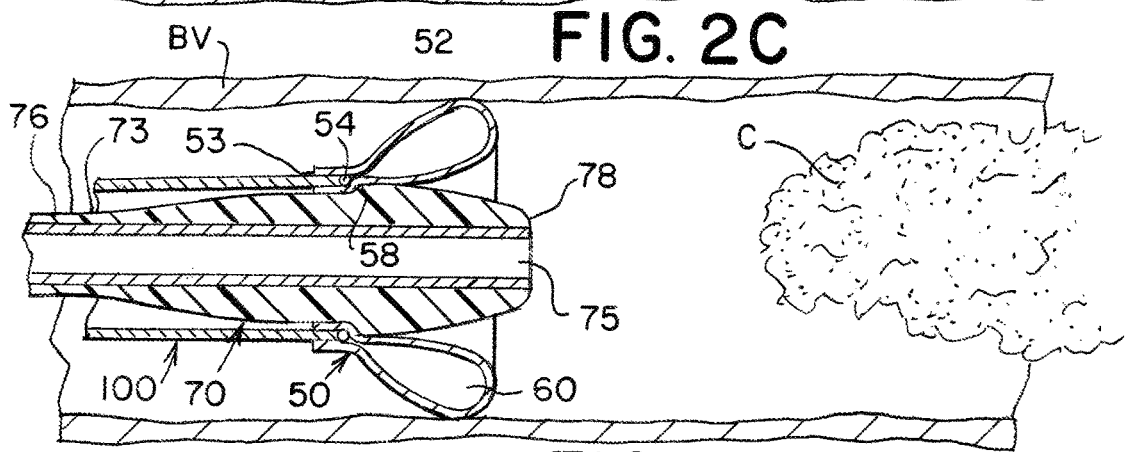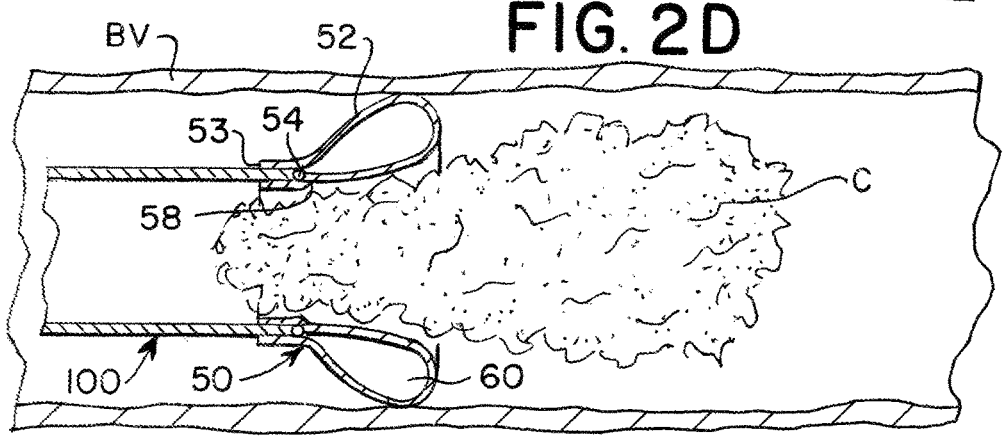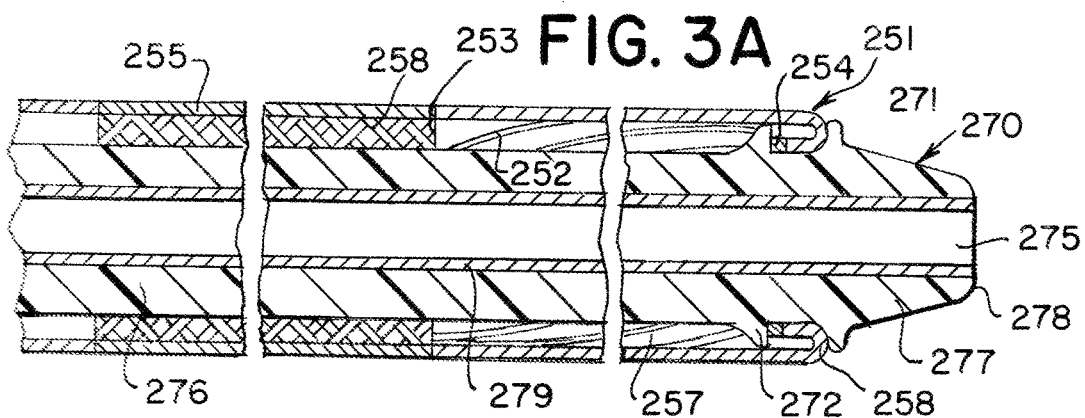

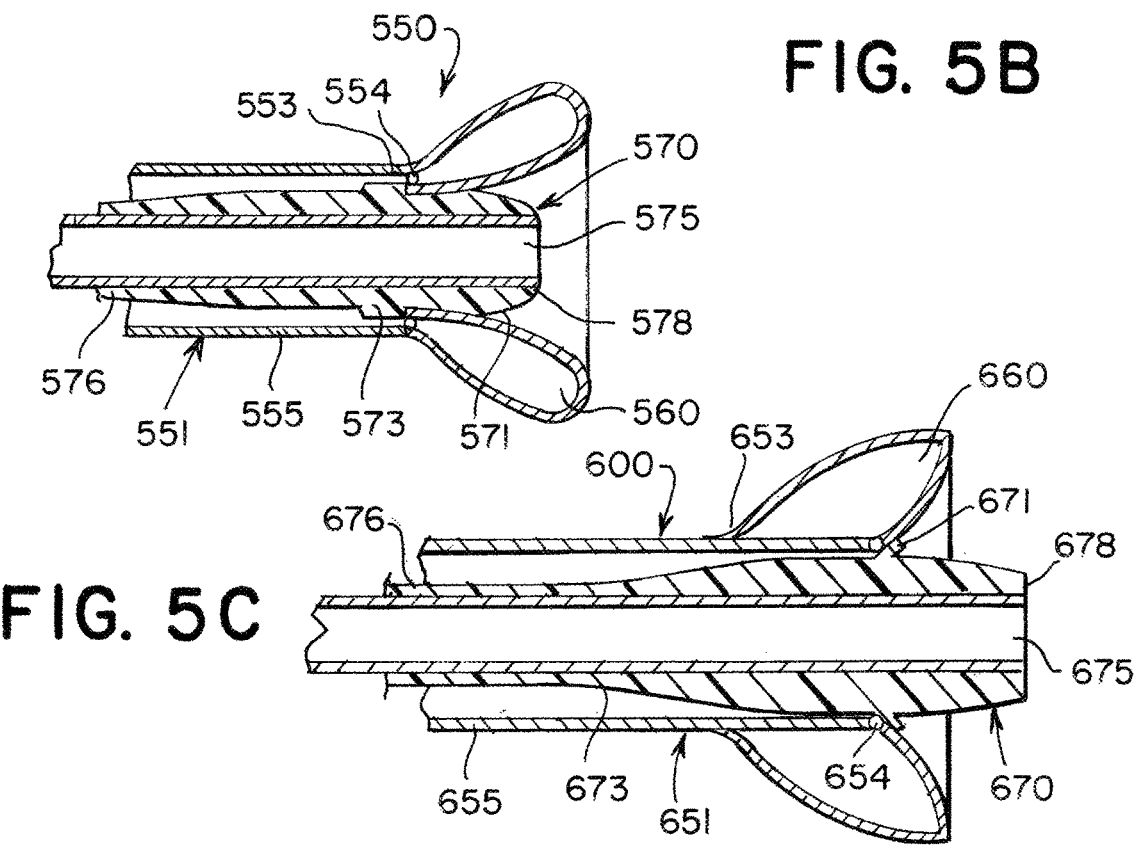
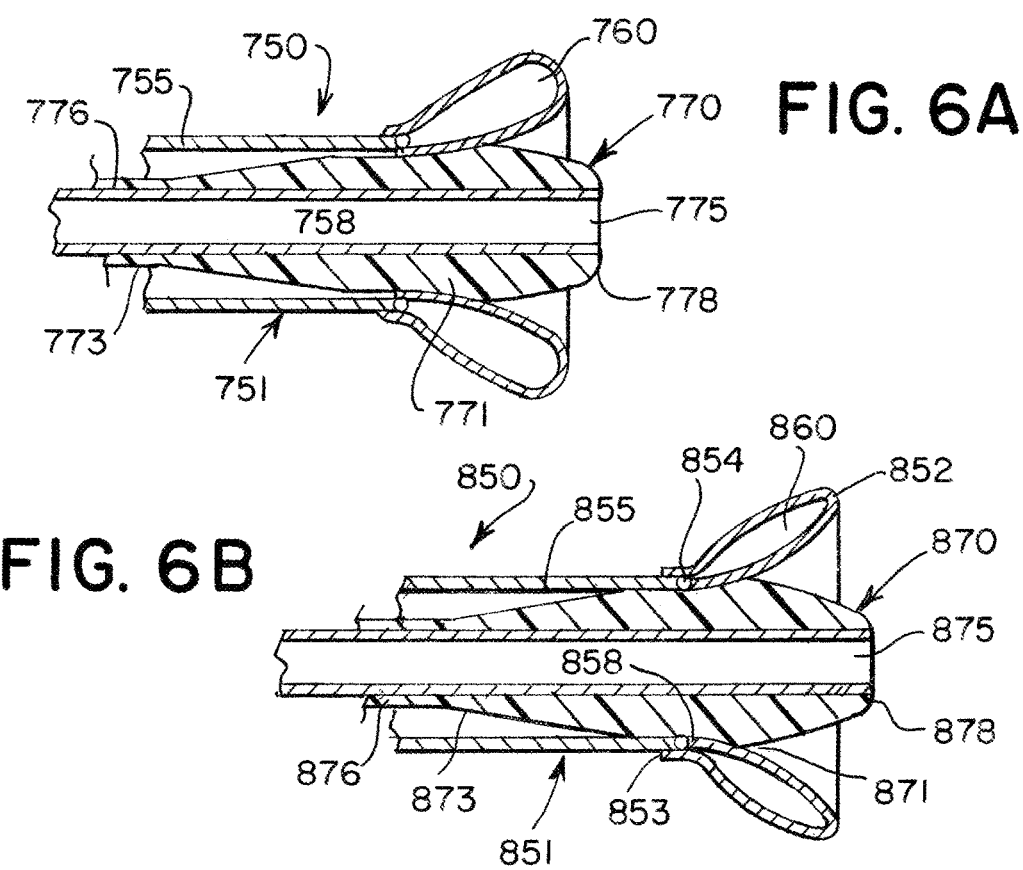

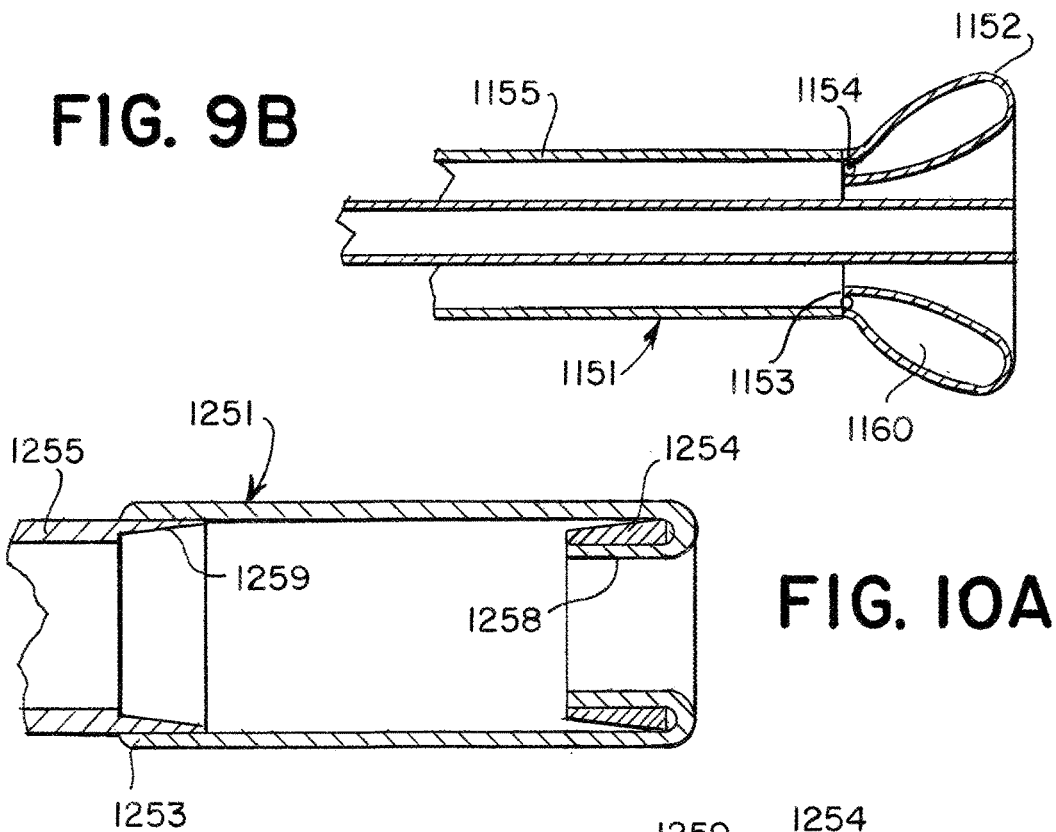
FIG. 9B
FIG. 10A
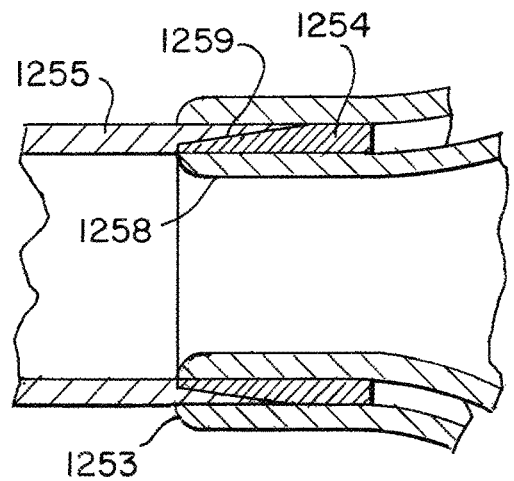
FIG. 10B
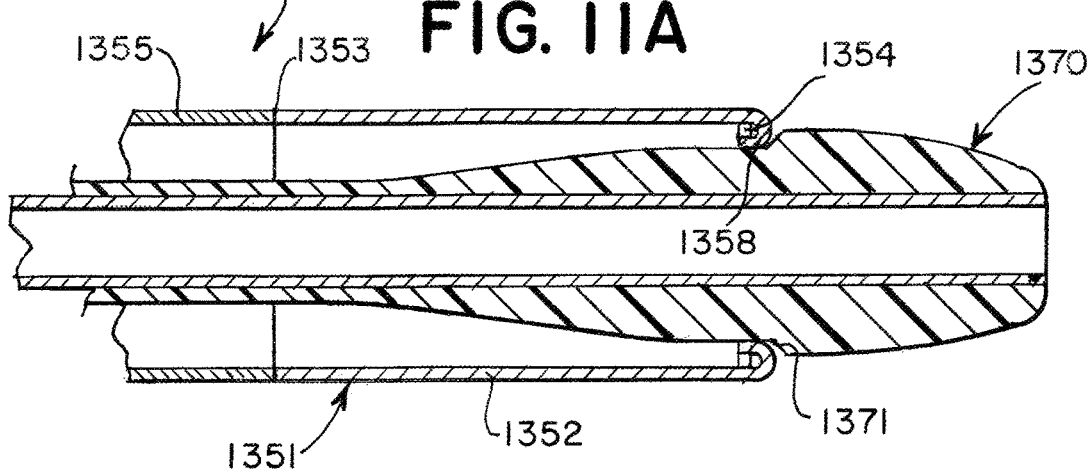
FIG. 11A

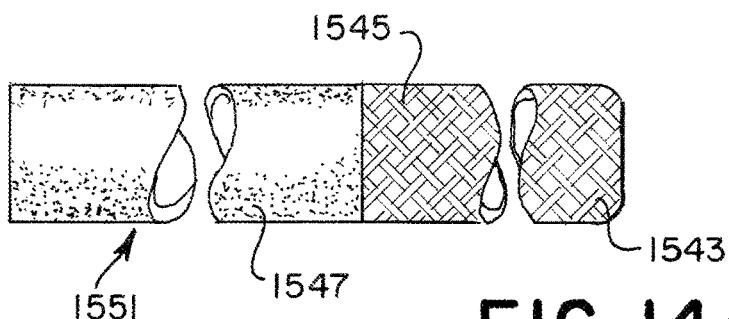
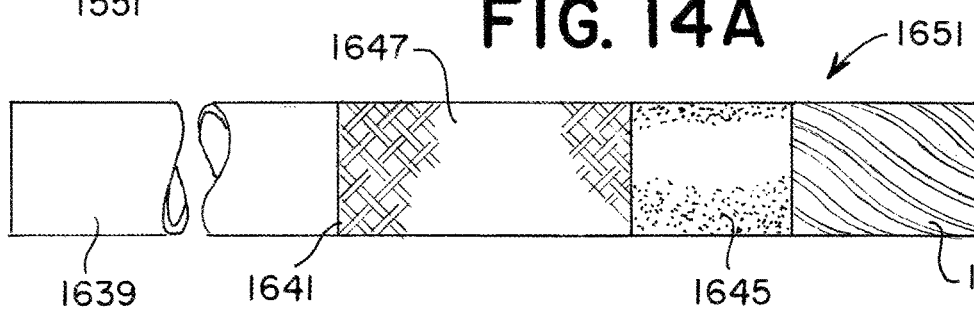
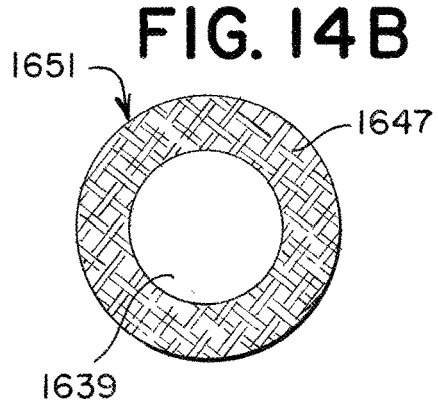
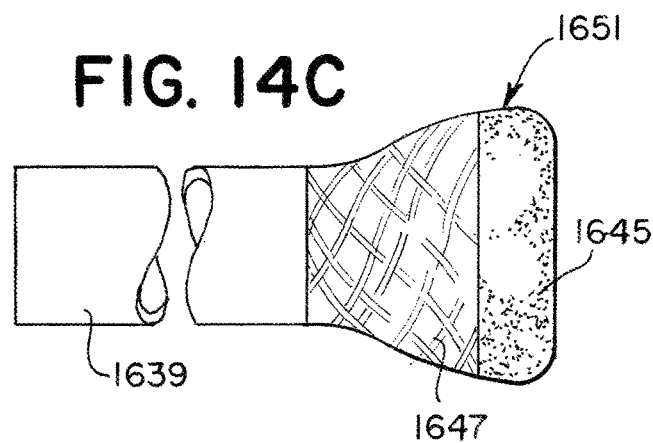
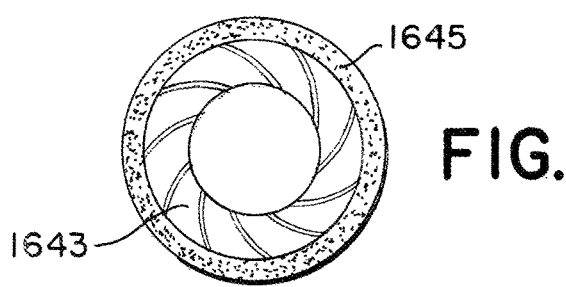
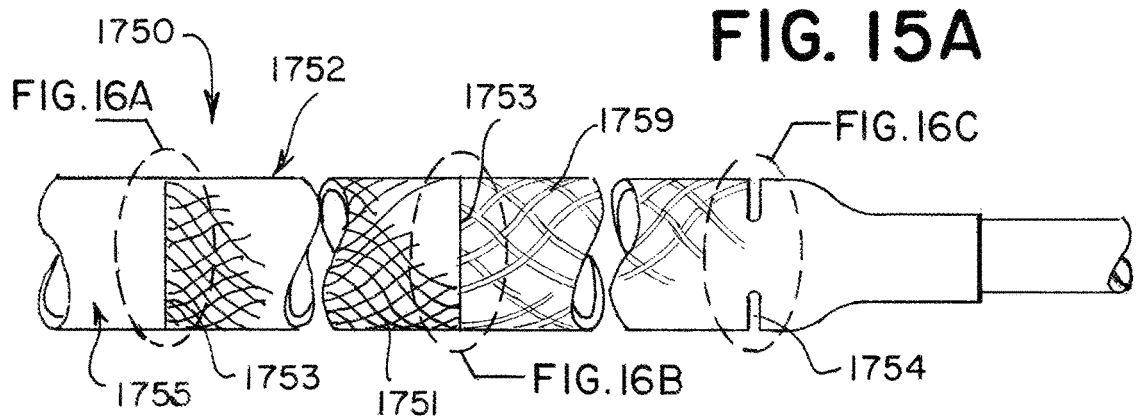

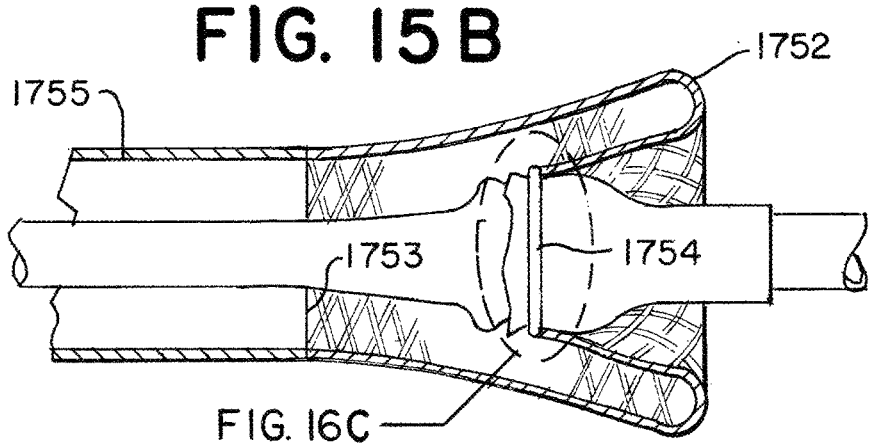
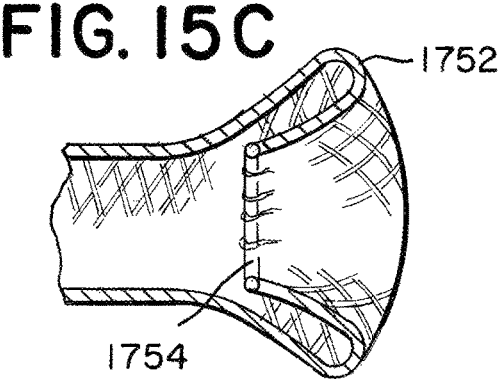
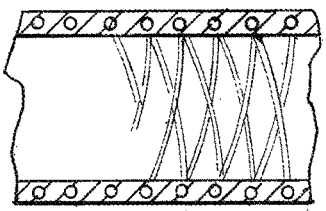
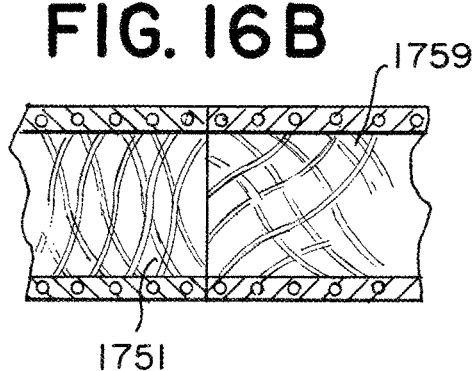
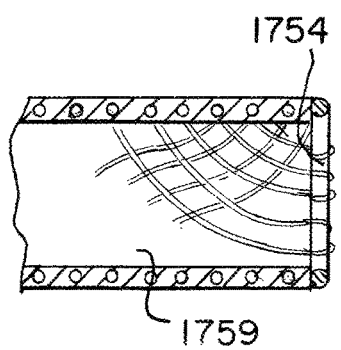
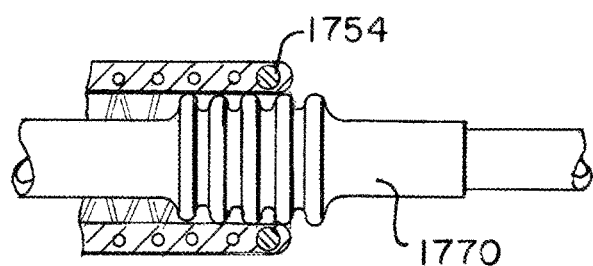

EXPANDABLE MOUTH CATHETER

CROSS-REFERENCE TO RELATED APPLICATION

This application claims the benefit of U.S. Provisional 62/898,864, filed Sep. 11, 2019, the contents which are herein incorporated by reference.

FIELD

The present disclosure generally relates to devices and methods for removing acute blockages from blood vessels during intravascular medical treatments. More specifically, the present disclosure relates to an expandable catheter used in aspiration of clots.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing remote areas such as the neurovascular bed is challenging with conventional technology, as the target vessels are small in diameter, distant relative to the site of insertion, and are highly tortuous.

The clot itself can complicate procedures by taking on a number of complex morphologies and consistencies, ranging from simple tube-shaped structures which assume the shape of the vessel to long, strand-like arrangements that can span multiple vessels at one time. The age of a clot can also affect its compliance, with older clots tending to be less compressible than fresh clots. Fibrin rich clots also present a challenge in having a sticky nature that can cause a clot to roll along the outer surface of a mechanical thrombectomy device rather than being gripped effectively. Combinations of soft and firm clot regions can also separate during aspiration, with fragmentation leading to distal embolization which can occur in vessels that cannot be reached with currently available devices. Additionally, breaking the bonds adhering the clot to the vessel wall without damaging fragile vessels is a significant challenge.

Conventional clot retrieval catheters, especially those for operating in the neurovascular, can suffer from a number of drawbacks. First, the diameters of the catheters themselves must be small enough to avoid causing significant discomfort to the patient. The catheter must also be sufficiently flexible to navigate the vasculature and endure high strains, while also having the axial stiffness to offer smooth advancement along the route. Once at the target site, typical objects to be retrieved from the body can be substantially larger in size than the catheter tip, making it more difficult to retrieve objects into the tip. For example, fibrin-rich clots can often be difficult to extract as they can become lodged in the tip of traditional fixed-mouth catheters. This lodging can cause softer portions of the clot to shear away from the firmer regions, leading to distal embolization.

Small diameters and fixed tip sizes can also be less efficient at directing the aspiration necessary to remove blood and thrombus material during the procedure. The aspiration suction must be strong enough such that any fragmentation occurring through the use of a mechanical thrombectomy device or other methods can, at the very least, be held stationary so that fragments cannot migrate and occlude distal vessels. When aspirating with a traditional fixed-mouth catheter, however, a significant portion of the aspiration flow ends up coming from vessel fluid proximal to the tip of the catheter where there is no clot. This significantly reduces aspiration efficiency, lowering the success rate of clot removal.

The disclosed design is aimed at providing an improved aspirating retrieval catheter which addresses the above-stated deficiencies.

SUMMARY

It is an object of the present design to provide systems, devices, and methods to meet the above-stated needs. The design features an expandable catheter with an expandable clot-facing mouth for flow restriction, aspiration efficiency, and easy retrieval of the clot while also having a collapsed state that is low-profile and sufficiently flexible for delivery in a standard sheath or outer catheter. The catheter can also have a tailored, variable-stiffness body section incorporating deliverability enhancements over existing designs and capable of navigating tortuous areas of the vasculature to reach an occlusive clot.

In some examples, a catheter system is disclosed that is actuatable to a deployed state. The system can include a catheter body with a lumen. A dilator can be positioned at least partially within the lumen, a distal end of the dilator being connected to a distal tip of the catheter body. The dilator can be retractable to expand and invert the distal tip to form a funnel shape in the deployed state.

In some examples, the distal tip can include a proximal segment and a distal segment extended from the proximal segment and being substantially flexible. A proximal end of the distal segment can be extended from the proximal segment and can include a pull ring adjacent and/or connected to a distal end of the distal segment.

In some examples, a midpoint of the distal segment in a collapsed state transitions to being a distalmost atraumatic end of the funnel shape in the deployed state distal of the catheter body.

In some examples, the distal segment in a collapsed state can be substantially tubular and in the deployed state can include the funnel shape. An air cushion can be formed by the funnel shape between the distal end and the pull ring.

In some examples, the distal segment can be divided into a proximal braid portion and a distal spiral portion.

In some examples, the dilator can include a proximal segment and a distal segment distal of the proximal segment can include a diameter greater than the proximal segment, the distal segment can include a contact element extended radially outward from the distal segment of the dilator and configured to contact and translate proximally the pull ring until being aligned at or adjacent the proximal end of the distal segment of the dilator.

In some examples, the contact element can include an interference fit with the distal end of the distal tip of the catheter body.

In some examples, the distal segment of the dilator can include a greatest diameter at the contact element and decreases from the contact element to the distal end of the distal segment.

In some examples, the distal segment of the dilator can include a greatest diameter at the contact element and tapers from the contact element to a junction between the proximal and distal segments of the dilator.

In some examples, the proximal segment of the dilator being highly flexible or substantially more flexible than the distal segment of the dilator.

In some examples, the dilator can include a substantially flexible segment extending distally of the stiffer distal segment, the substantially flexible segment being a short nose.

In some examples, the proximal segment of the dilator can include a fiber reinforcement system to negate elongation.

In some examples, the dilator can include a proximal segment and a distal segment distal of the proximal segment. The distal segment of the dilator can include a greatest diameter greater than the proximal segment. The distal segment of the dilator can include a distal contact element extended radially outward from the distal segment and configured to contact and translate proximally the pull ring until being aligned at or adjacent the proximal end of the distal segment. A proximal contact element of the dilator can be proximally spaced from the distal contact element and extended radially outward from the distal segment and configured to contact and translate proximally the pull ring, the proximal contact element can include a diameter less than the distal contact element. The pull ring can be connected between the contact elements.

In some examples, the pull ring can be positioned in a gap positioned between the contact elements.

In some examples, the contact element can include an interference fit with the distal end of the distal tip when in the funnel shape of the deployed state.

In some examples, at least one of the contact elements includes a magnetic connector operable to magnetically retract the distal tip to the funnel shape of the deployed state.

In some examples, the proximal segment and/or the distal segment of the dilator can include a substantially thinned wall.

In some examples, the proximal segment can include string-like filaments configured to prevent elongation under tension.

In some examples, the proximal segment of the distal tip can be stiffer than the distal segment.

In some examples, the distal segment can be stiffer than the proximal segment.

In some examples, the distal segment can include a resistance to remain in a substantially tubular shape prior to deployment.

In some examples, the proximal segment and/or the distal segment of the distal tip can include a braided structure.

In some examples, the proximal segment and/or the distal segment of the distal tip can include a memory alloy.

In some examples, the distal segment of the distal tip in a collapsed state can be substantially tubular and in the deployed state can include the funnel shape, an air cushion formed by the funnel shape between the distal end and the pull ring.

In some examples, the dilator can include a proximal segment and a distal segment distal of the proximal segment. The distal segment can include a distal contact element extended radially outward from the distal segment and configured to contact and translate proximally the pull ring until being aligned at or adjacent the proximal end of the distal segment of the distal tip. The pull ring can include a magnetic connector. The proximal end of the distal tip is magnetized configured to attract the pull ring thereby causing the distal tip to retract to the funnel shape.

In some examples, the proximal end of the distal tip and the pull ring are locked together in the deployed state, including, but not limited to, corresponding magnets locked together.

In some examples, the proximal end of the distal tip and the pull ring each include planar mating surfaces.

In some examples, the proximal end of the distal tip and the pull ring each include mating surfaces profiled with ridges and/or interlocking recesses.

In some examples, the proximal end of the distal tip and the pull ring each include mating surfaces tapered for a taper lock interaction.

In some examples, the proximal end of the distal tip and the pull ring each include mating surfaces configured to snap lock together.

In some examples, the pull ring includes a similar diameter to the catheter body such that an abutment is formed between the pull ring and catheter body in the deployed state. The distal tip can extend distally from an inner diameter of the pull ring and around an outer diameter of the pull ring to extend proximally over the catheter body.

In some examples, the distal tip can include a proximal segment and a distal segment extended from the proximal segment. The distal segment of the distal tip can be substantially flexible and include a proximal end positioned on an outer surface of the distal tip. The distal segment of the distal tip can include a pull ring adjacent or immediately distal thereof. The distal tip can be configured for interacting between the pull ring and a distal face of catheter body.

In some examples, the proximal end of the distal segment of the distal tip can be external to the pull ring.

In some examples, the distal tip can be integral with the catheter body. The distal tip can include a proximal segment and a distal segment extended from the proximal segment. The distal segment can be substantially flexible and include a proximal end substantially aligned with a pull ring internal thereto when configured in the funnel shape.

In some examples, the dilator can include a substantially tubular proximal segment and a distal segment distal of the proximal segment. The distal segment of the dilator can include a diameter greater than the proximal segment. The distal segment of the dilator can include a contact element extended radially outward from the distal segment and configured to contact and translate proximally the pull ring until being aligned at or adjacent a distal end of the proximal segment of the distal tip.

In some examples, the contact element can be an outward angled latch.

In some examples, the contact element can be an orthogonally outward latch.

In some examples, the contact element can be distal of the proximal end of the distal segment.

In some examples, a midpoint of the distal segment of the distal tip in a collapsed state transitions to being a distalmost petal tip of the funnel shape in the deployed state distal of the catheter.

In some examples, a midpoint of the distal segment of the distal tip in a collapsed state transitions to being a distalmost flower-like petal tip of the funnel shape in the deployed state distal of the catheter.

In some examples, the dilator can include a proximal segment and a distal segment distal of the proximal segment. The distal segment can include a distal contact element extended radially outward from the distal segment and configured to contact and translate proximally the pull ring until being aligned at or adjacent the proximal end of the distal tip.

In some examples, the dilator can include a proximal contact element tapering proximally from the distal contact element. The proximal contact element can include a diameter less than the distal contact element. In some examples, the distal contact element can be an outwardly extend ring-like member. In some examples, the distal contact element can include a semi-circle shape. In some examples, the distal contact element can be connected to the pull ring.

In some examples, a midpoint of the distal segment in a collapsed state transitions to being a distalmost petal tip of the funnel shape in the deployed state distal of the catheter.

In some examples, a midpoint of the distal segment in a collapsed state transitions to being a distalmost flower-like petal tip of the funnel shape in the deployed state distal of the catheter.

In some examples, the dilator can include a proximal segment and a distal segment distal of the proximal segment. The distal segment can include a greatest diameter greater than the proximal segment and can include a diameter larger than the proximal segment. A distal contact element can include a transition from the distal segment to the proximal segment and configured to contact and translate proximally the pull ring to cause an interference fit with the pull ring to transmit a force to expand the distal tip to the funnel shape.

In some examples, the distal tip is configured to first expand to a substantially conical shape before inverting to form the funnel shape.

In some examples, the proximal segment of the dilator is highly flexible and includes a thin wall.

In some examples, the proximal segment of the dilator is highly flexible and includes longitudinal string-like fibres to prevent it from stretching under tension.

In some examples, upon forming the inverted funnel shape, an interference force between the dilator and the pull ring is incapable of moving the pull ring proximally.

In some examples, the dilator tip can squeeze through the pull ring.

In some examples, the dilator tip is easily retracted through the catheter.

In some examples, the dilator tip can include a proximal segment and a distal segment extended from the proximal segment. The distal segment can be substantially flexible and be at least partially positioned around the proximal segment at least at a proximal end of the distal segment. The distal tip can include a pull ring, which can include an external taper matching an internal taper of the proximal segment such that tapers lock together when forming the funnel shape.

In some examples, the braid extends circumferentially at a mid point of the distal tip to aid in defining a rounded inversion seam.

In some examples, the braid extends from proximal to distal end of the distal tip thereby providing a rounded inversion seam.

In some examples, the braid includes a subset of filaments extended from proximal to middle portions so that the filaments revert to extend back to the proximal portion forming a looped braid pattern, and the remaining filaments extend from a proximal end to a distal end such that a spiral portion is formed distal of the looped subset of filaments.

In some examples, the braid includes filaments extended from proximal to distal portions in a helical configuration.

In some examples, the braid includes an inversion hinge in or around the middle portion.

In some examples, the proximal portion can be relatively stiff. The middle portion can be relatively flexible, and the distal portion can include a flexible helix.

In some examples, the distal tip can include a braid with proximal, middle and distal portions, wherein the distal portion includes sufficient radial force to push the proximal portion radially outwardly while being configured to accommodate various vessel sizes in an atraumatic manner.

In some examples, a method of inverting an expansile catheter in a blood vessel is disclosed. The method can include advancing the catheter to a target site; and retracting, by a dilator at least partially within a lumen of the catheter, a distal tip of the catheter, causing the distal tip to expand and invert to a funnel shape.

In some examples, the method can include restricting, by the funnel shape, flow in the blood vessel.

In some examples, the method can include withdrawing the dilator from the catheter; aspirating through the catheter to stimulate a thrombus into a mouth of the funnel shape; and withdrawing the catheter with the captured thrombus from the patient.

In some examples, the method can include capturing the occlusive thrombus with a mechanical thrombectomy device; and withdrawing the thrombectomy device into the funnel shape of the catheter.

In some examples, the dilator may not be required. In such approaches, the collapsed tip can be corked onto the clot and aspiration suction force can pull the distal end proximally to invert the tip and create the inverted funnel shape during aspiration.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

FIG. 2B depicts the expansile tip of an expansile catheter of FIGS. 1A-1C, deployed to a target location, according to aspects of the present disclosure.

FIG. 2C depicts the expansile tip of an expansile catheter of FIGS. 1A-1C, deployed to a target location, according to aspects of the present disclosure.

FIG. 2D depicts the expansile tip of an expansile catheter of FIGS. 1A-1C, deployed to a target location, according to aspects of the present disclosure.

FIG. 3A depicts an expansile tip of an expansile catheter in a first configuration with a dilator of this disclosure.

FIG. 5B depicts an expansile tip of an expansile catheter in the deployed configuration with a dilator of this disclosure.

FIG. 5C depicts an expansile tip of an expansile catheter in the deployed configuration with a dilator of this disclosure.

FIG. 6A depicts an expansile tip of an expansile catheter in the deployed configuration with a dilator of this disclosure.

FIG. 6B depicts an expansile tip of an expansile catheter in the deployed configuration with a dilator of this disclosure.

FIG. 9B depicts the expansile tip in the deployed configuration of FIG. 9A with the dilator removed.

FIG. 10A depicts an expansile tip of an expansile catheter in a first configuration, according to aspects of the present disclosure.

FIG. 10B is a close-up of the expansile tip of FIG. 10A in the deployed configuration, according to aspects of the present disclosure.

FIG. 11A depicts an expansile tip of an expansile catheter in a first configuration with a dilator of this disclosure.

FIG. 13 depicts a side view of an expansile tip of an expansile catheter in one configuration according to this disclosure.

FIG. 14A depicts a side view of an expansile tip of an expansile catheter in one configuration according to this disclosure.

FIG. 14B depicts a rear view of the expansile tip of FIG. 14A in another configuration according to this disclosure.

FIG. 14C depicts a side view of the expansile tip of FIG. 14B according to this disclosure.

FIG. 14D depicts a front view of the expansile tip of FIG. 14B according to this disclosure.

FIG. 15A depicts a side view of an expansile tip of an expansile catheter in one configuration according to this disclosure.

FIG. 15B depicts a close-up view of the expansile tip of FIG. 15A according to this disclosure.

FIG. 15C depicts a close-up view of the expansile tip of FIG. 15A according to this disclosure.

FIG. 16A depicts a close-up view of the expansile tip of FIG. 15A according to this disclosure.

FIG. 16B depicts a close-up view of the expansile tip of FIG. 15A according to this disclosure.

FIG. 16C depicts a close-up view of the expansile tip of FIG. 15A according to this disclosure.

FIG. 16D depicts a close-up view of the expansile tip of FIG. 15A according to this disclosure.

DETAILED DESCRIPTION

The objective of the solution of this disclosure is an invertible, expansile catheter capable of providing both local flow restriction/arrest with a large distal facing mouth and a tailored, highly flexible body section capable of navigating tortuous areas of the vasculature to reach an occlusive clot. Flow restriction and large tipped designs offer substantially greater aspiration efficiency. Such advantages can also be especially beneficial in the case of stroke intervention procedures, where vessels in the neurovascular bed are particularly small and circuitous, and as a result a tailored axial and bending stiffness profile can inhibit kinking and binding. The catheter can also be compatible with relatively low-profile access sheaths and outer catheters, so that a puncture wound in the patient's groin (in the case of femoral access) can be easily and reliably closed. The catheter can also feature internal and/or external low-friction liners, and an outer polymer jacket or membrane disposed around the support structure.

These improvements can lead to safe and more rapid access of a catheter and other devices to complex areas in order to remove occlusions and shorten procedure times. While the description is in many cases in the context of mechanical thrombectomy treatments, the systems and methods may be adapted for other procedures and in other body passageways as well.

Accessing the various vessels within the vascular system, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures. When these products are employed in conjunction with the system and methods of this disclosure in the description below, their function and exact constitution are not described in detail.

Figure 1A:
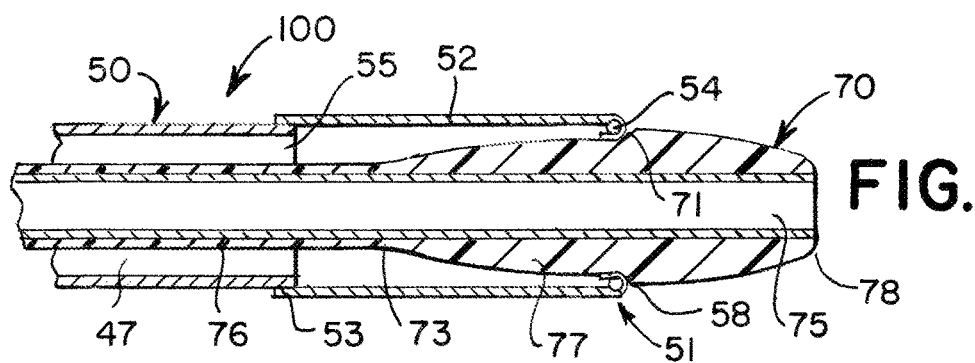
FIG. 1A depicts an expansile tip of an expansile catheter in a first configuration with a dilator of this disclosure.
Figure 1B:
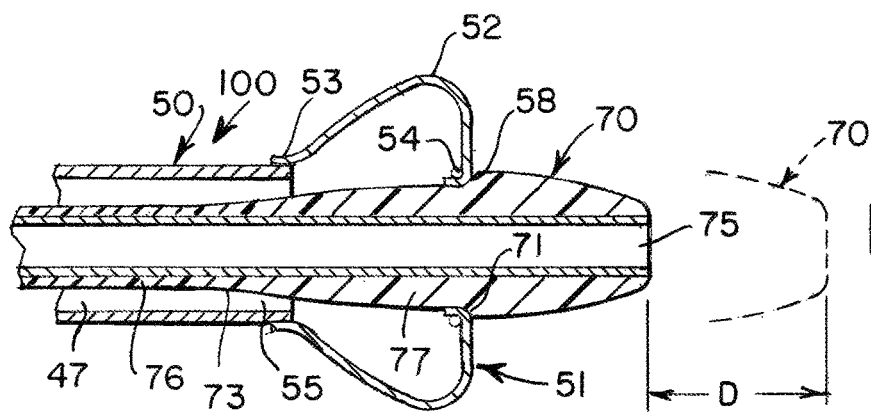
FIG. 1B depicts the expansile tip of the expansile catheter in another configuration with the dilator of FIG. 1A.
Figure 1C:
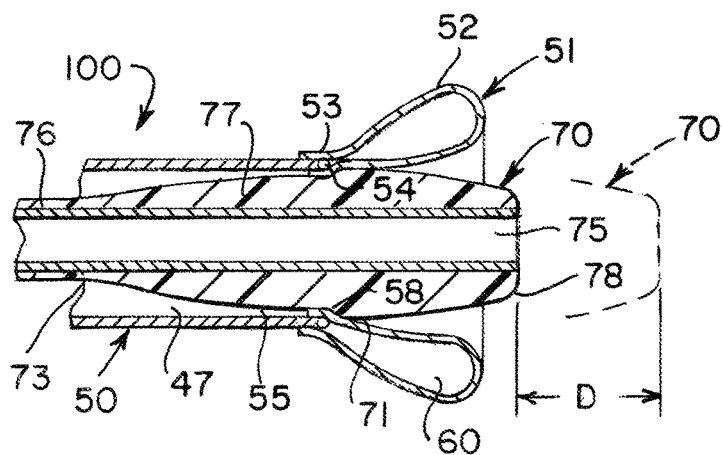
FIG. 1C depicts the expansile tip of the expansile catheter in another configuration with the dilator of FIG. 1A.
Figure 2A:
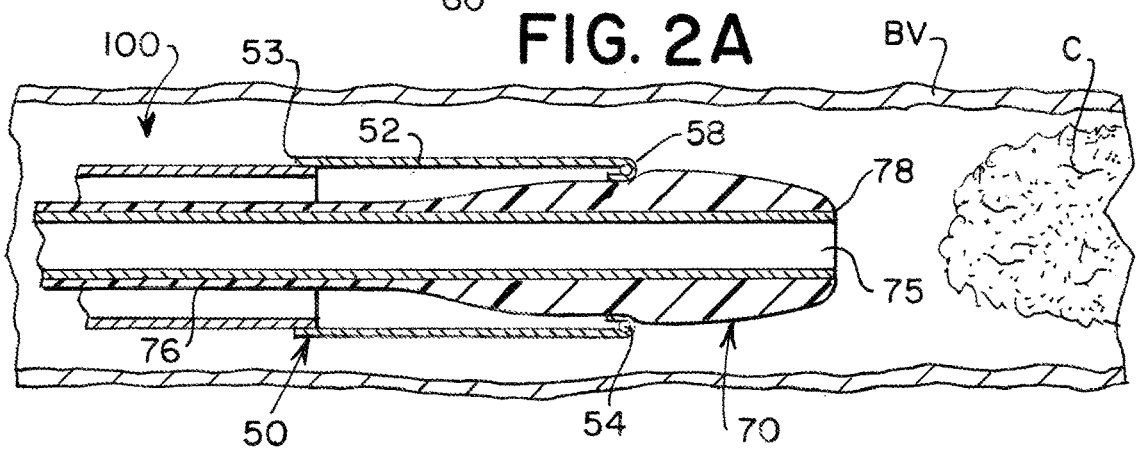
FIG. 2A depicts the expansile tip of an expansile catheter of FIGS. 1A-1C, deployed to a target location, according to aspects of the present disclosure.

Referring to the figures, in FIGS. 1A-1C there is illustrated a catheter system 100 for removing an occlusive clot C (shown in FIGS. 2A-2D) from a vessel BV of a patient. System 100 can be an aspiration catheter of traditional construction or can have rapid-exchange (RX) type features, many of which can greatly increase the speed and efficiency of the clot retrieval procedure. In particular, FIGS. 2A-2D illustrate catheter body 50 of catheter 100 deployed to a target blood vessel BV, according to aspects of the present disclosure. System 100 can be actuatable to a deployed state, which is shown in FIG. 1C. A dilator 70 can be positioned at least partially within the lumen 47 of the catheter body 50. A distal end 78 of the dilator 70 can be connected to a distal tip 51 of the catheter body 50. The dilator 70 can be retractable to invert the distal tip 51 and form a funnel shape in the deployed state, as shown with system moving proximally one or more distances D from an initial elongate state of FIG. 1A to deployed in FIG. 1C. While FIG. 1C does show the deployed state, dilator 70 would be fully removed prior to aspiration in order to maximize the flowrate possible through the catheter body of tip 51 and also to allow passage of a microcatheter and stentriever. Dilator 70 may also include a distally protruding microcatheter portion such that a stentriever could be uncovered across the clot during activation of the funnel and removal of the dilator 70.

For an OD of approximately 2 mm catheter body in an M1, the ratio of collapsed OD to deployed funnel OD is contemplated to range between approximately 2.5 mm to 4.0 mm. At the carotid T, the ratio is contemplated to range 4.0 mm to 6.0 mm. Where the ratio is contemplated to range 5.0 to 8.0 mm, the ratio is feasible for ICA vessel placement. Where the ratio is contemplated to range 2.5 to 5.0 mm, the ratio is envisaged to target M1 and Carotid T locations.

In some examples, a ratio between the collapsed OD to funnel OD is dependent on the length of the corresponding catheter tip when collapsed. Preferably, the tip collapsed length can be range between 3 mm and 8 mm (e.g., the distances D in the figures) for expanded ODs of approximately 2.5 mm to 5.0 mm. Yet, in some examples, the ratio can be a function of the diameter the braid is set at and the braid angle.

System 100 can be configured to expand to a wide range of target vessel diameters, such as a carotid terminus (3.2-5.2 mm), a horizontal M1 segment of the Middle Cerebral Arteries (1.6-3.5 mm), and/or the Internal Carotid Artery (ICA, 2.7-7.5 mm). If the catheter system 100 is then retracted from an M1 segment to the ICA (or another route with a proximally increasing vessel inner diameter), the radial force of the tip 50 once in the funnel shape can continue to seal with the vessel across a range of vessel sizes. Further, a tip 50 capable of a range of target vessel diameters can also seal at vessel bifurcations which can have a wider cross-sectional area than the vessel proximal and vessels distal to the bifurcation. Preferably, the tip 51 is inverted to the deployed funnel shape at the treatment location to avoid having to advance a funnel-shaped catheter tip through the vasculature.

The ideal nominal diameter of the catheter system 100 depends on the location of the target clot and/or a diameter of any other catheter through which catheter system 100 is to be delivered. For retrieval of clots in the intracranial vessels of the cerebral vascular bed, where vessel diameters at the M1 locations are commonly around 3 mm, an applicable system can have an outer catheter with an inner diameter of 0.065" to 0.080" and an RX clot retrieval catheter with an inner diameter of 0.055"-0.070". Upon deployment, the maximum diameter of the tip 50 can be a minimum of 2.5 mm (but in some instances up to 8 mm), allowing it to seal against the walls of the vessel and providing a funnel-shape distal mouth as large as the vessel itself. In some instances, the tip 51 can also provide an opening large enough to oppose bifurcations and/or proximal vessel locations. This seal, in combination with a maximized proximal lumen of the disclosed RX system over a conventional catheter, offers benefits in terms of aspiration force at the face of the clot and increased flowrates with a design that utilizes the larger inner diameter of the outer catheter.

In some examples, distal tip 51 can include a proximal segment 55 and a distal segment 52 extended from the proximal segment 55. Segment 52 can be substantially flexible and a proximal end 53 of the distal segment 52 can be extended from the proximal segment 55 and include a pull ring 54 adjacent and/or connected to a distal end 58 of the distal segment 52. Pull ring 54 in this example can be positioned on a proximal face 54 of the distal end inside the distal segment 52. In this respect, segment 52 can be an expandable sheath attached under pull ring 54.

A midpoint of the distal segment 52 in the collapsed state, as in FIG. 1A, can transition to being a distalmost atraumatic end of the funnel shape in the deployed state, as in FIG. 1C, distal of the catheter body 50, as dilator 70 moves proximally a distance D while connected to distal end 58. Distal segment 52 in a collapsed state can be substantially tubular (FIG. 1A) whereas in in the deployed state after proximally moving distances D (FIG. 1B, FIG. 1C) segment 52 can include the funnel shape.

In some examples, the funnel shape formed by the inverted distal segment 52 can include an air cushion 60 formed between the distal end 58 and the pull ring 54. In some examples of the funnel shape, ring 54 can be positioned inside the lumen 47 to form a compression lock therewith thereby securing segment 52 in its expanded, funnel shape. The compression lock can be defined as the interference fit by fitting the ring 54 within lumen 47 whose inner diameter may be slightly less than the outer diameter of ring 54.

In some examples, the distal segment 52 can be divided into a proximal braid portion and a distal spiral braid portion. An elastomeric membrane can be interlaced, coated thereon, or extend over the braid or inverting frame structure. For example, an elastic membrane can follow the contours of the underlying braided strut framework of tip 51. The elastic membrane can at least partially run the length of tip 51. In other examples, tip 51 can be further coated with a lubricious material such as commercially available hydrophilic coatings (e.g., Surmodics, Harland, Biocoat, Covalon) or may include low friction materials or fillers. The membrane can also float over the inverting support structure such that the inverting structure struts can move freely under the membrane. In some examples, the membrane incapsulates the inverting support structure.

In some examples, dilator 70 can include a proximal segment 76 and a distal segment 77 distally extended thereof. Segment 77 can include a diameter greater than the proximal segment 76 and include a contact element 71 extended radially outward to contact and translate proximally the pull ring 54 one or more distances D until being aligned at or adjacent the proximal end 53 of the distal segment 52. In this example, contact element 71 can be a sudden, angled outward transition that creates a contact surface that forms an interference fit with distal end 58 of segment 52.

In some examples, dilator 70 can be solid and/or hollow with a lumen therein. Dilator 70 can include an inner lumen 75 be substantially elongate (e.g. tubular) at its proximal segment 76 and taper radially, outwardly to distal segment 77 with distal end 78 having a larger diameter than the proximal segment 76. This taper can commence at a transition or junction 73 between segments 76, 77. Dilator 70 can be highly flexible proximal to tip 51. Dilator 70 can include one or more fibers as part of its structure that are configured for reinforcement to negate elongation thereof. In some examples, segment 76 can be highly flexible or substantially more flexible than the distal segment 77. The distal segment 77 in some examples can still have adequate flexibility to contort around tortuous vasculature. Any stiff portions required to transmit force to ring 54 can be kept as short as possible to maintain lateral flexibility of the tip 51.

In one example, system 100 can use an aspiration source to capture a clot, as shown in FIGS. 2A-2D. In particular, FIGS. 2A-2D show system 100 being deployed and then aspirating clot C, preferably with dilator 70 fully removed as in FIG. 2D. The main advantage of using dilator 70 as shown and described is that it can be removed after inversion of the tip such that the full cross-sectional area of catheter 50 can be used to maximize flow rate and force on the clot C through catheter body 50 when in the funnel shape, as shown. As also shown in FIGS. 2A-2D, the funnel shape formed by tip 51 being expanded can seal with the walls of the blood vessel BV or the seal or seals can be selectively activated (e.g., by moving dilator 70 proximally or distally).

Tip 51 once expanded can include a large, atraumatic mouth for efficient aspiration. Tip 51 can include kink-resistant characteristics to aid in advancing it to the target location. It can therefore have multiple configurations, or be fabricated from multiple materials, as discussed herein, so as to maintain lateral flexibility but avoid expanding or kinking in compression. The large distal mouth of tip 51 shown in FIGS. 2A-2D can offer improved performance over conventional fixed-mouth designs, which can be hindered by having firm, fibrin-rich clots lodge in the tip and/or by having softer portions of the clot shear away. It is less likely for clots to become lodged in the tubular section of the disclosed invertible, expansile tip 51 due to the progressive compression of the clot upon entry to the reducing funnel shape.

Struts of the tip 51 can be formed from Nitinol or another shape-memory material with sufficient elastic strain capacity such that the elastic limit would not be exceeded when the tip is constrained and delivered in the collapsed configuration within an outer catheter or during expansion to invert to a funnel shape. The struts can be heat set expanded only to promote inversion at a predetermined location, said expanded area being restrained by an outer membrane covering. Actively inverting in this respect the frame then pushes the membrane outwardly by increasing the radial force of the frame. In another case, the framework can be constructed from wire, allowing a non-superelastic material like a stainless-steel alloy to be employed, since the wires would be free to move independent of one another. It is appreciated that a framework of tip 51 constructed of wire using superelastic or shape memory materials can also be envisaged, such a device offering improved torque and durability characteristics. In another case, a framework of tip 51 can be laser cut or formed with wire from a non-superelastic or shape memory material that accommodates strain by including cells or bends, with a lower degree of strain required to move from a collapsed state for delivery to an expanded state for clot retrieval. For example, the framework can include additional cells, longer cell struts, and/or lower cell angles to reduce strain requirements.

Figure 3B:
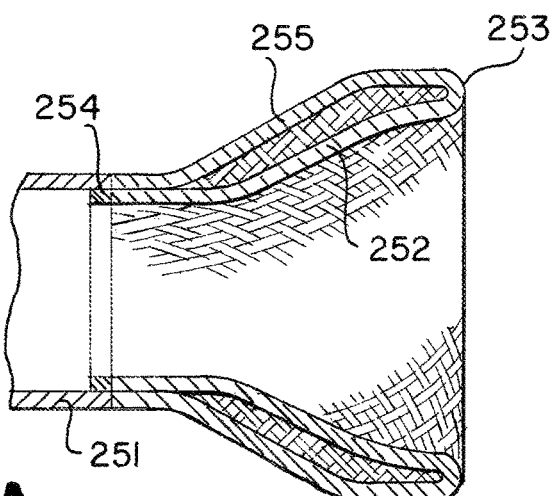
FIG. 3B depicts the expansile tip of the expansile catheter in another configuration with the dilator of FIG. 3A.

FIGS. 3A-3B depicts another invertible, expansile tip 251 going from a first configuration, shown in FIG. 3A, with dilator 270 and then a close-up of the funnel-shape, deployed configuration of tip 251 in FIG. 3B without dilator 270. While not shown, dilator 270 could be included in FIG. 3B as needed or required. It is understood that similar reference numbers examples discussed throughout this disclosure indicate identical or functionality similar elements. With that, dilator 270 can include inner lumen 275 with proximal segment 276 and distal segment 277 terminating in distal end 278 distal of the proximal segment 276. Dilator 270 can include distal contact element 271 extended radially outward from the distal segment 277. Element 271 can be configured to contact and translate the pull ring 254 until being aligned at or adjacent the proximal end 258 of the distal segment 252. Dilator 270 may also include a sudden, angled outward transition (e.g., element 271 here being substantially orthogonal to the outer surface of dilator 270) to form a contact surface that forms an interference fit with distal end 258 of segment 252. Dilator 270 can also have a proximal contact element 273 proximally spaced from the distal contact element 271 and similarly extended radially outward from the distal segment 277. In some examples, a groove can be defined between elements 271, 273 in which the pull ring 254 can be positioned or otherwise connected. In this respect, opposed faces of the space or groove between elements 271, 213 can be planar or otherwise conform to the shape of ring 254. In some examples, element 271 can urge or otherwise couple to end 258 while element 273 can urge or otherwise couple to ring 254. In some examples, element 273 can include a diameter less than element 271, or vice versa. From element 271 to distal end 278, dilator 270 can taper to a smaller diameter.

As in system 100, an interference fit can be provided in catheter body 250 between distal end 258 of the distal tip 251 when in the funnel shape of the deployed state. In some examples, at least one of the contact elements 271, 273 can include a magnetic connector operable to magnetically retract the distal tip 251 to the funnel shape of the deployed state. In so doing, the magnetic coupling therein can facilitate the actuation of tip 271 into the inverted, funnel-shape of the deployed state. Segment 276 and/or the segment 277 can include a substantially thinned wall. Preferably, going from segment 276 to segment 277, dilator can include a relatively thin wall proximal to tip for optimum flexibility.

Segment 276 in some examples can include string-like filaments configured to prevent elongation under tension. With respect to tip 251, its proximal segment 255 can be stiffer than the distal segment 252. However, this example is not so limited and instead segment 252 can be stiffer than the proximal segment 255. In some examples, segment 252 can include a resistance or bias to remain in its substantially tubular shape prior to deployment, as in FIG. 3A. Proximal segment 255 and/or distal segment 252 can also include a braided structure, similar to segments 152, 155. For examples, segments 252, 255 can be constructed from a framework of struts that include a memory alloy. Similar to segment 52, segment 252 can be divided into a proximal braid portion and a distal spiral braid portion as well include one or more elastomeric coating(s) or membrane(s). The braid and spiral portions of this example can be created, for example, by finishing the ends of the clockwise braid wires at a midpoint between the ends of the counterclockwise braid wires such that the counterclockwise braid wires form a spiral past this point. In some examples, this can be achieved by cutting the clockwise wires of a standard braid on a circumferential plane at a location between the ends of the braid. In another example, clockwise braids can be looped to extend proximally such that a denser proximal braid is paired with a distal spiral portion.

Figure 4A:
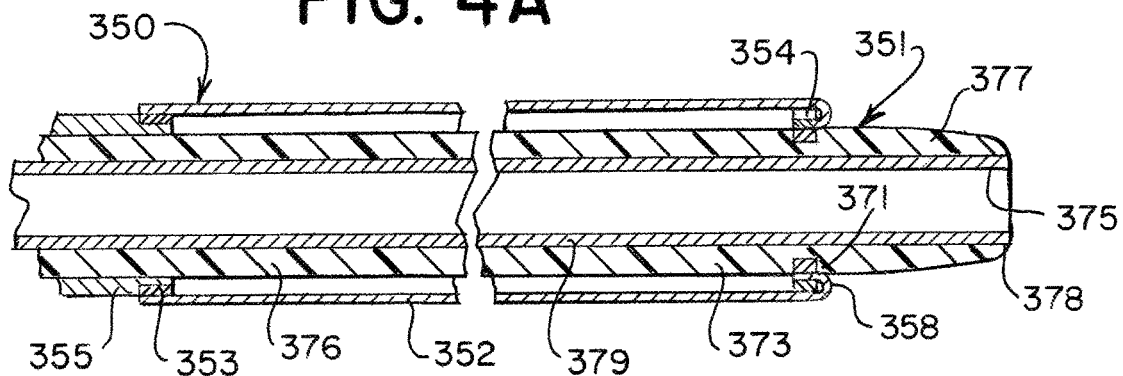
FIG. 4A depicts an expansile tip of an expansile catheter in a first configuration with a dilator of this disclosure.
Figure 4B:
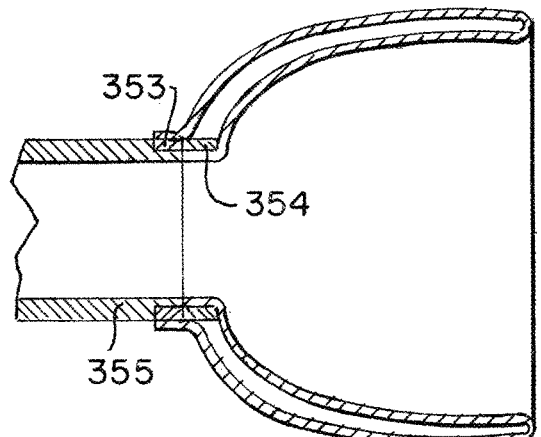
FIG. 4B depicts the expansile tip of the expansile catheter in another configuration with the dilator of FIG. 4A.

FIGS. 4A-4B depicts another invertible, expansile tip 351 of catheter 350 going from a first configuration, shown in FIG. 4A, with dilator 370 and then a close-up of the funnel-shape, deployed configuration in FIG. 4B, after dilator 370 has been retracted to invert tip 351 to the funnel-shape. In this instance, proximal segment 355 of tip 351 can include a distal end 353 that can include a magnetic element capable of coupling with corresponding ring 354, which in turn can be magnetized. Ring 354 as shown can be configured to magnetically couple with end 353 so tip 351 can maintain the inverted, funnel shape shown in FIG. 4B. In some examples, ring 354 and/or end 353 can be made from a ferrous metal such that one is attracted to the other. Alternatively, both features are magnetic such that the south pole of one engages with the north pole of the other to form a stronger engagement than if a ferrous metal was used. In yet another embodiment, dilator 370 can include magnetic features to engage with the pull ring 354 to provide sufficient force to invert tip 351 to its inverted, funnel-shape.

In some examples, dilator 370 can include inner lumen 575, distal segment 377 terminating in distal end 278 distal of the proximal segment 376, with each including similar diameters. Contact element 371 of dilator 370 can be a distal end of a notch or gutter or groove or recess of dilator whereas contact element 372 can be the proximal end of the same notch or gutter or groove or recess. In some examples, element 371 can be magnetic so as to grip ring 354 (e.g., by constructing ring 354 out of one or more ferrous materials), and pull ring 354 proximally during retraction of the dilator 370. Ring 354, which can be coupled to end 358, can be positioned therebetween respective to said notch or gutter or groove or recess and/or therearound. As arranged, distal segment 377 translate pull ring 354 until being aligned at or adjacent the proximal end 358 of the distal segment 352 thereby inverting segment 352 to form the atraumatic funnel-shape of FIG. 4B. In some examples, the proximal end 353 of the distal tip 351 and the pull ring 354 can be locked together in the deployed state by the corresponding magnetic coupling therebetween. The proximal end 353 of the distal tip 351 and the pull ring 354 can each include planar mating surfaces or mating surfaces profiled with ridges and/or interlocking recesses. For example, mating surfaces can be tapered for an interlocking taper lock interaction. In other examples, mating surfaces can be configured to snap lock together.

Figure 5A:
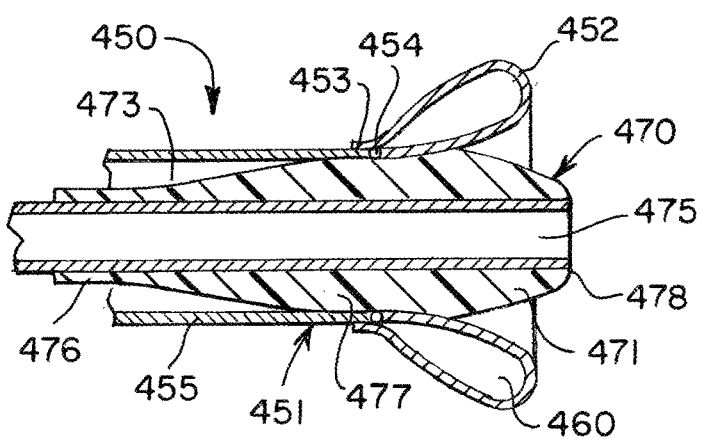
FIG. 5A depicts an expansile tip of an expansile catheter in the deployed configuration with a dilator of this disclosure.

FIG. 5A depicts another invertible, expansile tip 451 of catheter 450 with dilator 470. Tip 451 can include proximal segment 455 and distal segment 452 extended from the proximal segment 455 and being substantially flexible. A proximal end 453 of the distal segment 452 can be positioned on an outer surface of the distal tip 451. Similar to previously described tips, a pull ring 454 can be adjacent or immediately distal of segment 455 so ring 454 can be used to pull and cause segment 452 to invert to the funnel-shape of FIG. 5A. In some example, proximal end 453 of the distal segment 452 can be external to the pull ring 454. Aligning ring 454 in this respect and attaching proximal end 453 as shown to the OD of catheter 450 and position membrane structure attached to distal face of pull ring. In turn, this attachment allows membrane to smoothly taper distally when inverted.

FIG. 5B depicts another invertible, expansile tip 551 of catheter 550 with dilator 570 of this disclosure. Distal tip 551 as shown can be integral with the catheter body 550, including segment 555 being integral with segment 552.

Dilator 570 of this example can also include a greatest diameter at or around contact element 573, which here can be an outward bulge or ring-like extrusion configured to be arranged internal to ring 554 and form an interference fit with element that distally tapers from element 573. As shown, ring 554 fits under catheter body 550, the proximal face of membrane structure is in line with or integral with distal face of catheter body 550, and the membrane structure is attached under pull ring 554. In turn, this attachment allows membrane to smoothly taper distally when inverted.

FIG. 5C depicts another invertible, expansile tip 651 of catheter 650 in the deployed configuration with dilator 670. As shown, dilator 670 can include a distal segment 677 distal of the proximal segment 676 with a diameter greater than the proximal segment 676. The change in diameter can be gradual to form an elliptical or otherwise curved shape. Distal segment 677 can include a contact element 671 extended radially outward from the distal segment 677 and configured to contact and translate proximally the pull ring 654 until being aligned at or adjacent a distal end of the proximal segment 655. Element 671 as can be seen can be an outward angled latch. For example, element 671 as shown can include be angled distally so as to form an acute angle between it and the outer surface of dilator 670. This latch in turn can prevent the distal end of segment 652 from disengaging therefrom in the funnel-shape, as shown.

FIG. 5C depicts another invertible, expansile tip 651 of catheter 650 in the deployed configuration with dilator 670. As shown, dilator 670 can include inner lumen 675, a distal segment 677 with distal end 678 distal of the proximal segment 676 with a diameter greater than the proximal segment 676. The change in diameter can be gradual to form an elliptical or otherwise curved shape. Distal segment 677 can include a contact element 671 extended radially outward from the distal segment 677 and configured to contact and translate proximally the pull ring 654 until being aligned at or adjacent a distal end of the proximal segment 655. Element 671 as can be seen can be an outward angled latch. For example, element 671 as shown can include be angled distally so as to form an acute angle between it and the outer surface of dilator 670. This latch in turn can prevent the distal end of segment 652 from disengaging therefrom in the funnel-shape, as shown.

FIG. 5C depicts another invertible, expansile tip 651 of catheter 650 in the deployed configuration with dilator 670. As shown, dilator 670 can include inner lumen 675, a distal segment 677 with distal end 678 distal of the proximal segment 676 with a diameter greater than the proximal segment 676. The change in diameter can be gradual to form an elliptical or otherwise curved shape. Distal segment 677 can include a contact element 671 extended radially outward from the distal segment 677 and configured to contact and translate proximally the pull ring 654 until being aligned at or adjacent a distal end of the proximal segment 655. Element 671 as can be seen can be an outward angled latch. For example, element 671 as shown can include be angled distally so as to form an acute angle between it and the outer surface of dilator 670. This latch in turn can prevent the distal end of segment 652 from disengaging therefrom in the funnel-shape, as shown.

Element 671 is not so limited, however, and can instead by substantially orthogonal with respect to the outer surface of dilator 670. Element 671 may also be distal of the proximal end 653 of segment 652, whereby end 653 can be positioned on an outer surface of segment 655. In some examples, a midpoint of the distal segment 652 in a collapsed state transitions to being a distalmost petal tip of the funnel shape in the deployed state distal of the catheter 650. System 600 in this respect can include one continuous petal or a plurality of radially separated distalmost flower-like petal tips that form the funnel shape. In other examples, the funnel-shape of system 600 can be more pointed, or less atraumatic than the rounded funnel-shapes of FIGS. 5A-5B.

FIG. 6A depicts another invertible, expansile tip 751 of catheter 750 in the deployed configuration with a dilator 770 of this disclosure. As shown, contact element 771 of dilator 770 is distal of and attached to tip 751 and provides a relatively smooth transition for clot capture and/or use of a stentriever therein. By arranging dilator 770 as shown with respect to tip 751, the inner diameter of system 700 being reduced on account of distal end 758 of segment 752 being positioned at least partially inside the inner diameter of system 700. Advantageously, the proximal face of pull ring 754 abuts the distal face of the catheter body 750 and the membrane/framework can be attached under the pull ring 754. In this example, the proximal membrane structure is attached to the OD of catheter 750 which allows the membrane to smoothly taper distally when inverted.

FIG. 6B depicts another invertible, expansile tip 851 of catheter 850 in the deployed configuration with a dilator 870 of this disclosure. As shown, contact element 871 of dilator 870 is distal of and attached to tip 851. Here, since end 858 of segment 852 is coaxial with segment 855 in the deployed, funnel-shape, the inner diameter between segments 855, 852 is substantially similar, if not equivalent. As shown, tip 851 can also include a relatively sharper edge in the funnel-shape, as compared to tip 751. Here, advantageously the proximal face of ring 854 abuts the distal face of the catheter body 850 and the membrane/framework is attached to the distal face of ring 854. Moreover, this causes a sharper inversion of funnel and the proximal membrane structure attached to an OD of catheter 750.

Figure 6C:
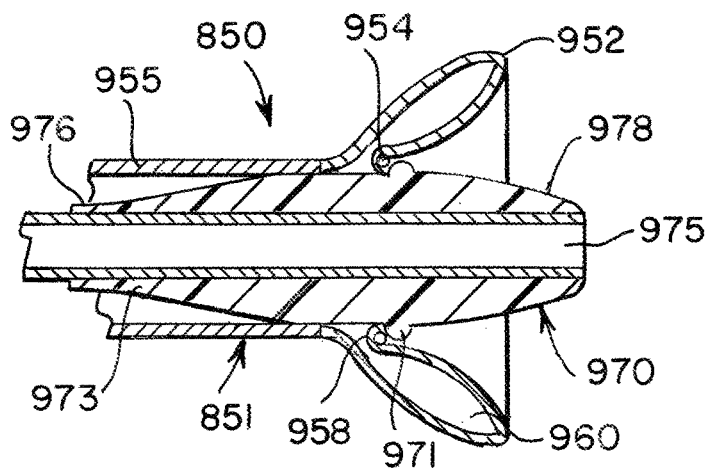
FIG. 6C depicts an expansile tip of an expansile catheter in the deployed configuration with a dilator of this disclosure.

FIG. 6C depicts another invertible, expansile tip 951 of catheter 950 in the deployed configuration with a dilator 970 of this disclosure. As shown, contact element 971 of dilator 970 is distal of and attached to tip 951. In particular, distal contact element 971 extended radially outward from the distal segment 977 and configured to contact and translate proximally the pull ring 954 until being aligned at or adjacent the proximal end 953 of the distal tip 951. A proximal end face of element 971 can be arranged to contact ring 954, which can be on a distal face of distal end 958 of segment 952. Here the proximal face of ring 954 abuts the distal face of the catheter body 950 and the membrane/ framework is attached to the distal face of ring 954 and a relatively sharper inversion of funnel results.

As shown, end 958 can have a biased curve that facilitates contact between ring 954 and end 958. In the funnel-shape configuration shown, the curve can extend proximally before returning distally to urge ring 954 to couple with the proximal face of element 971. In some examples, element 971 can include or be an outwardly extend ring-like member. Element 971 can also include a semi-circle shape.

Figure 7A:
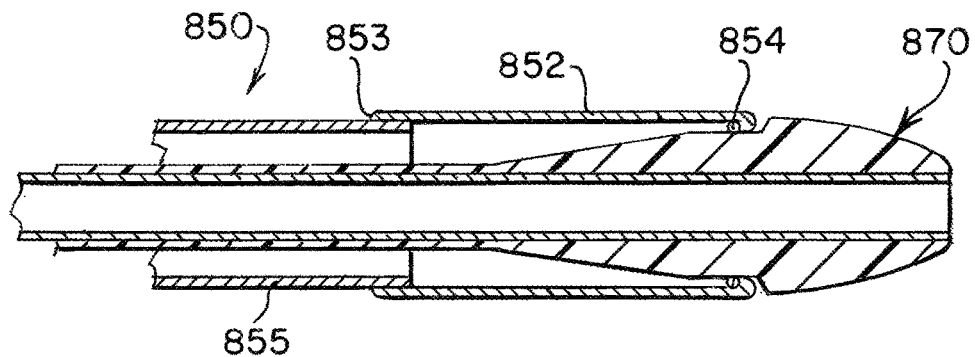
FIG. 7A depicts the expansile tip of an expansile catheter of FIG. 6B, being deployed according to aspects of the present disclosure.
Figure 7B:
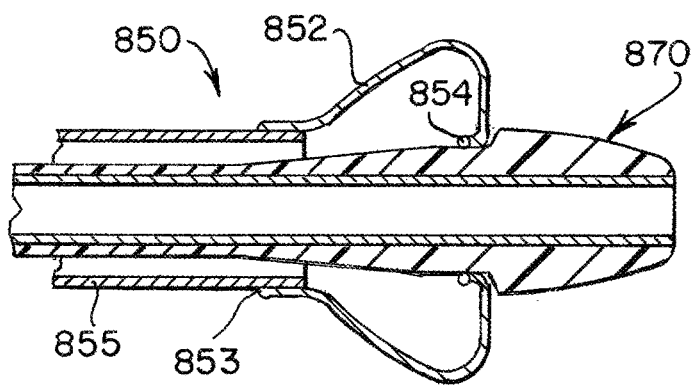
FIG. 7B depicts the expansile tip of an expansile catheter of FIG. 6B, being deployed according to aspects of the present disclosure.
Figure 7C:
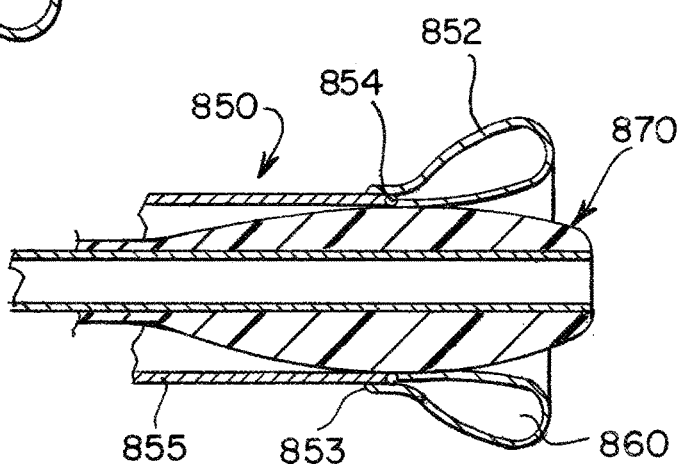
FIG. 7C depicts the expansile tip of an expansile catheter of FIG. 6B, being deployed according to aspects of the present disclosure.

FIGS. 7A-7C illustrates tip 851 but with a modified, sharper funnel-shape, previously described in FIG. 6B, transitioning from the collapsed, tubular state of FIG. 7A to the deployed, funnel-shape of FIG. 7C. In particular, dilator 870 is seen coupled to ring 854 at its respective contact element. FIG. 7B shows dilator 870 having been retracted a first distance causing segment 852 to initiate its expansion as its midsection begins inverting. FIG. 7C shows ring 854 having been proximally translated by dilator 870 until contacting the distal face of segment 855. In turn, segment 852 is completely inverted to the funnel-shape. Here, ring 854 has a similar diameter to segment 855 such that an abutment is formed between the ring 854 and segment 855 in the expanded state. Advantageously, this minimal difference in inner and outer diameters between the proximal and distal ends of catheter 850 optimizes its relatively low outer profile and large inner diameter.

Figure 8A:
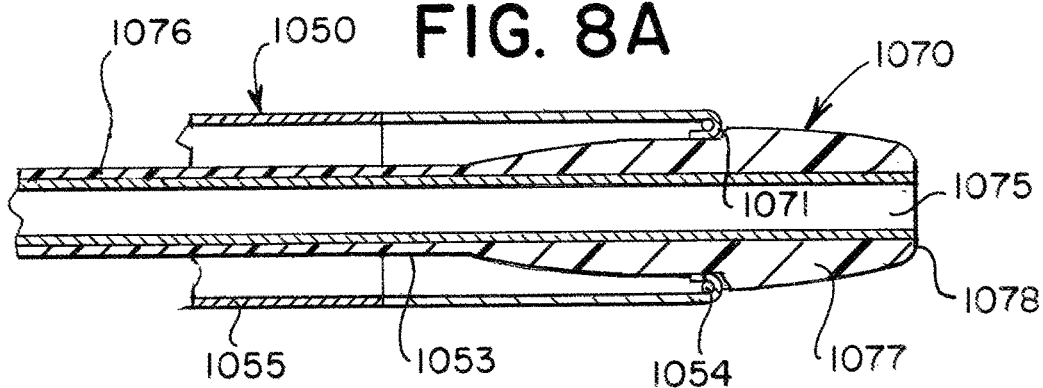
FIG. 8A depicts the expansile tip of an expansile catheter being deployed according to aspects of the present disclosure.
Figure 8B:
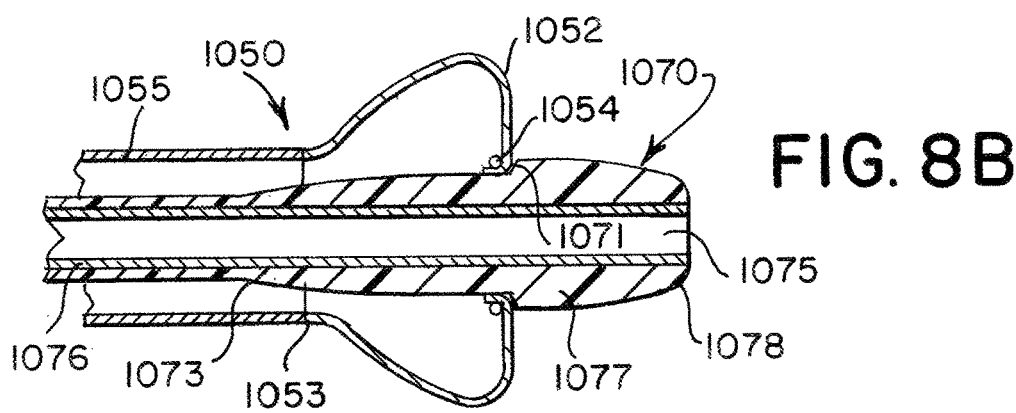
FIG. 8B depicts the expansile tip of an expansile catheter of FIG. 8A, being deployed according to aspects of the present disclosure.
Figure 8C:
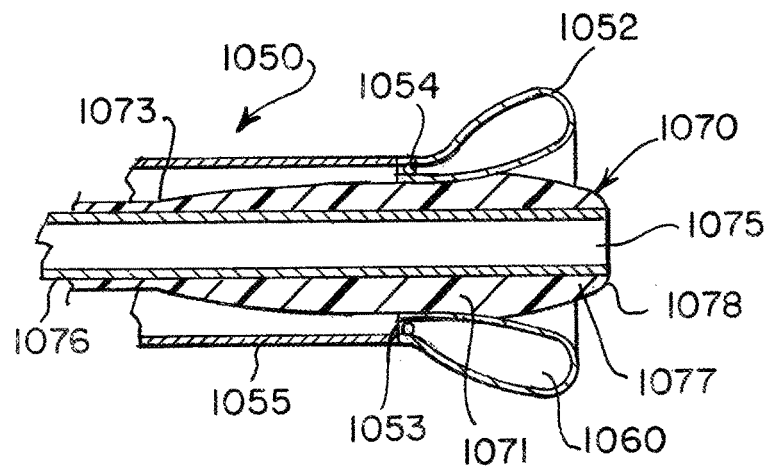
FIG. 8C depicts the expansile tip of an expansile catheter of FIGS. 8A-8B, being deployed according to aspects of the present disclosure.

FIGS. 8A-8C illustrates another expansile, invertible tip 1051 of catheter 1050 of this disclosure being deployed by being inverted in connection with dilator 1070, according to aspects of the present disclosure. In particular, tip 1051 is shown transitioning from the collapsed, tubular state of FIG. 8A to the deployed, funnel-shape of FIG. 8C. A proximal face of element 1071 is coupled to ring 1054. FIG. 8B shows dilator 1070 having been retracted a first distance causing segment 1052 to initiate its expansion as its midsection begins inverting. In the state of FIG. 8B, segment 1052 can include a generally conical shape before inverting. FIG. 8C shows ring 1054 having been proximally translated by dilator 1070 until be arranged proximate the distal face of segment 1055 (e.g., here, internal to segment 1055). In turn, segment 1052 is completely inverted to the funnel-shape shown in FIG. 8C. Ring 1054 can have a diameter to less than an inner diameter of segment 1055 such that an abutment is formed between the ring 1054 and the inner surface of segment 1055 in the expanded state.

In some examples, segment 1077 of dilator 1070 can be ultra soft to provide sufficient interference with pull ring 1054 to transmit a radial force sufficient to cause segment 1052 to expand and invert, as shown between FIGS. 8A-8C. In some examples, segment 1076 can be highly flexible so that it does not contribute significantly to stiffness of system. To achieve this, segment 1076 can include a relatively thin wall and may include longitudinal string-like fibers to prevent it from stretching under tension.

In some examples, once the inverted funnel shape shown in FIG. 8C has been formed, the interference force between the dilator 1070 and ring 1054 can be insufficient to move ring 1054 more proximally and the tip of dilator 1070 (e.g., segment 1077) squeezes through ring 1054. As segment 1077 is sized to have a small clearance with the lumen of segment 1055, segment 1077 can be easily retracted through the catheter system 1000. In some examples, dilator 1070 can be re-advanced to push ring 1054 distally and un-invert the funnel-shape to a collapsed, tubular sheath of FIG. 8A. In some examples, though not shown, a second stiffer dilator may be supplied for the purpose of collapsing tip 1051, once inverted and expanded within a blood vessel, where the first dilator 1070 may be present.

Figure 9A:
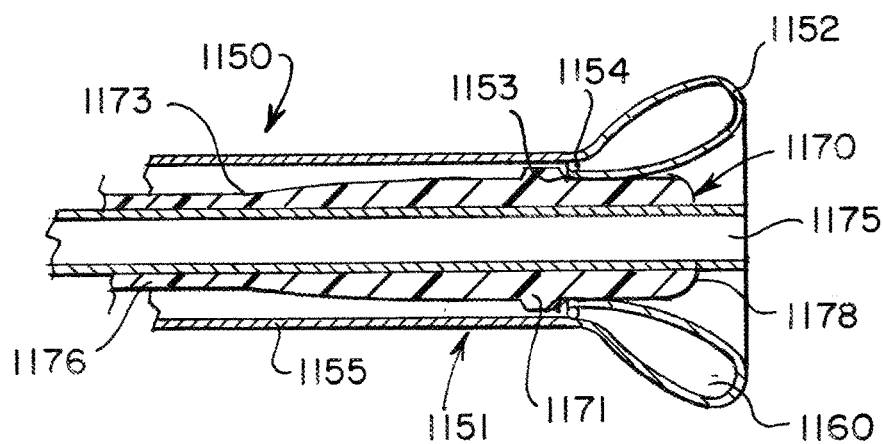
FIG. 9A depicts an expansile tip of an expansile catheter in the deployed configuration with a dilator of this disclosure.

FIGS. 9A-9B illustrate another expansile, invertible tip 1151 of catheter 1150. In particular, FIG. 9A shows tip 1151 with dilator 1170 in the expanded, funnel-shape configuration. FIG. 9B shows tip 1151 in the same configuration but with dilator 1170 having been retracted and removed from tip 1151. Here, the distal face of element 1171 is coupled to the proximal face of end 1158 so that tip 1151 is compressed through ring 1154. In turn, an inner diameter of end 1158 is coupled to ring 1154. In this example, coupling end 1158 to ring 1154 as described and shown allows tip 1151 to form a gradual smooth curve for entry of aspirated clot and or stent retriever devices. Moreover, ring 1154 being sized smaller than main catheter body inner diameter of segment 1155 allows for the pull ring 1054 to wedge or lock in position as segment 1177 of dilator 1170 compresses through it.

FIGS. 10A-10B illustrates tip 1251, according to aspects of the present disclosure, whereby FIG. 10A shows the tip 1251 when extended in the tubular configuration and FIG. 10B is a close-up of tip 1251 ring 1254 has been retracted to cause segment 1252 to expand and invert to the funnel shape. Ring 1254 can include an external taper that matches an internal taper 1259 positioned at a distal end of segment 1255. As shown more clearly in in FIG. 10B which shows the closed up of the coupled tapers, the corresponding tapers can couple and/or lock together. While only tapered surfaces are shown in FIGS. 10A-10B, it is contemplated that other interlocking surfaces can be used as needed or required.

Figure 11B:
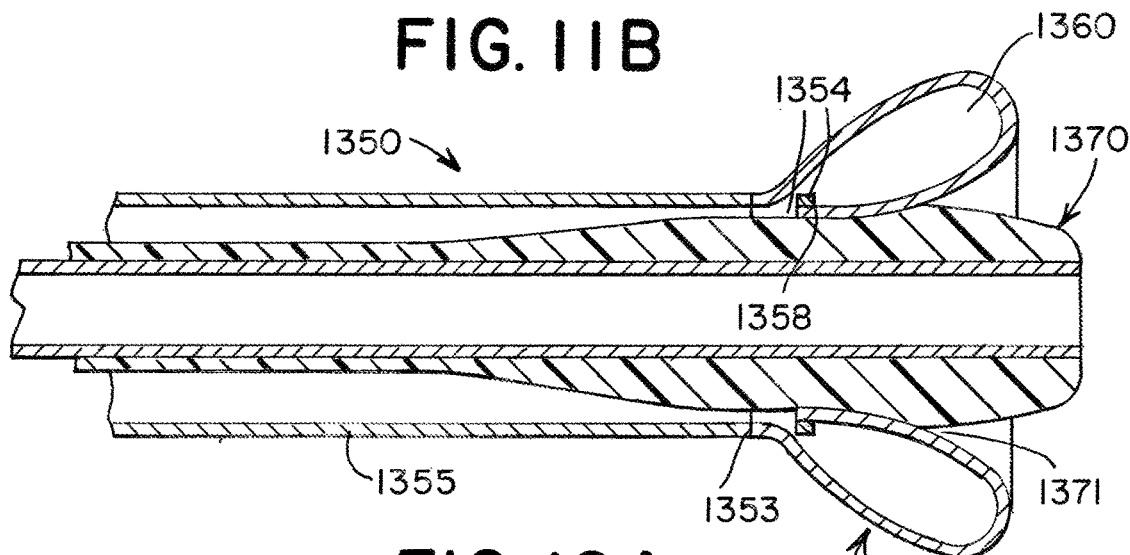
FIG. 11B depicts the expansile tip of the expansile catheter in another configuration with the dilator of FIG. 11A.

FIGS. 11A-11B depicts another expansile tip 1351 of catheter 1350 going from a first, tubular configuration in FIG. 11A with dilator 1370 and then to the expanded, inverted funnel-shape, deployed configuration of FIG. 11B. Dilator 1370 can include a contact element 1371 that includes the greatest diameter of dilator 1370 and then progressively, distally tapers therefrom for gradual radial compression of clot. Here, ring 1354 can include a similar diameter to the diameter of segment 1355 such that an abutment therebetween can prevent ring 1354 from moving proximally into the lumen of segment 1355, as shown in FIG. 11B. Distal end 1358 of segment 1352 is attached within an inner diameter of ring 1354, which provides the interference fit between end 1358 and/or ring 1354 with element 1371 of dilator 1370. Advantageously, in this example there is less of a difference in inner diameter between segment 1355 and ring 1354 such that clots can be less restricted from entering the lumen of segment 1355.

Further, by folding segment 1352, as shown, to extend distally from the inner diameter of ring 1354 and reverting to extend proximally over the outer diameter of ring 1354, segment 1353 can expand and invert to form a rounded feature for atraumatic funnel configured to interact and seal with a vessel wall.

If tip 1351 were manufactured to be stiff, it would form too large a round profile and have the potential of kinking when collapsed for delivery through an outer balloon guide or long guide sheath. Kinking can also prevent tip 1351 from forming a gradual taper in the deployed, funnel-shape configuration and may form a snag point for stentrievers during retraction in the catheter lumen. Therefore, configuring tip 1351 with a flexible portion can allow it to first form a soft compressible rounded feature in the collapsed configuration that will recover to form a progressive taper extending distally form the inner diameter of ring 1354 to aid in compression of clot during aspiration and to provide an unhindered path for collapsing a stentriever during retraction into the catheter lumen.

Figure 12A:
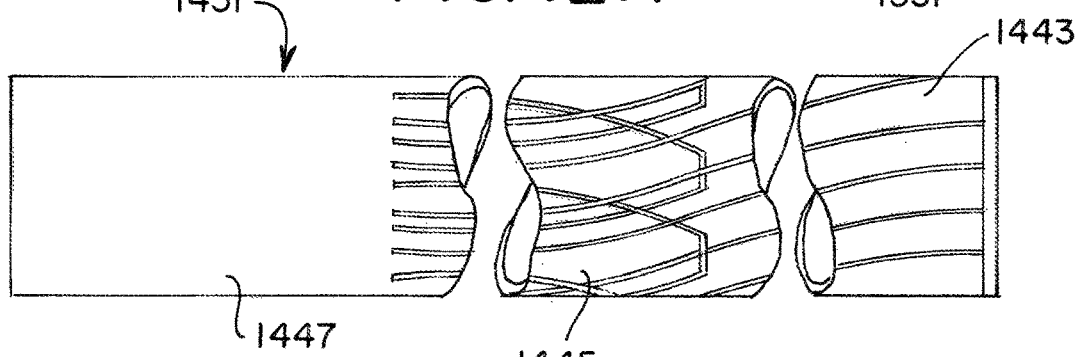
FIG. 12A depicts a side view of an expansile tip of an expansile catheter in one configuration according to this disclosure.

FIG. 12A depicts an example construction of one expansile, invertible tip 1451, which can include a braid with proximal 1447, middle 1445, and distal 1443 segments. Middle segment 1445 can include filaments that extend from proximal to a transition point with distal segment 1443, then they revert to extend back proximally forming a braid pattern. Distal segment 1443 can include filaments that extend from proximal to distal in a helical configuration and/or can include sufficient radial force to push proximal segment 1447 radially outwardly while being conformable to accommodate various vessel sizes in an atraumatic manner. A helical pattern can allow for a wider range of vessel size range than a braid as the helical wires will create a spiral pattern that can adjust more easily than a braid pattern. Distal segment 1443 can extend circumferentially at or around the transition between segments 1445, 1443 to aid in defining a less rounded inversion seam at the vessel wall.

Figure 12B:
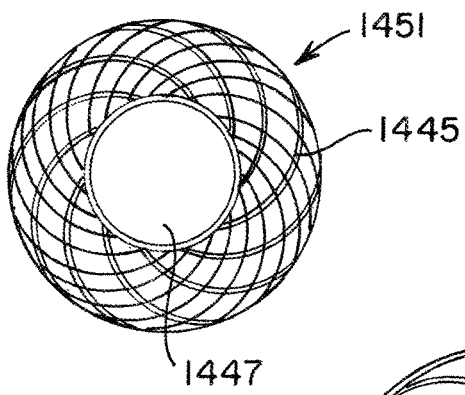
FIG. 12B depicts a rear view of the expansile tip of FIG. 12A in another configuration according to this disclosure.
Figure 12C:
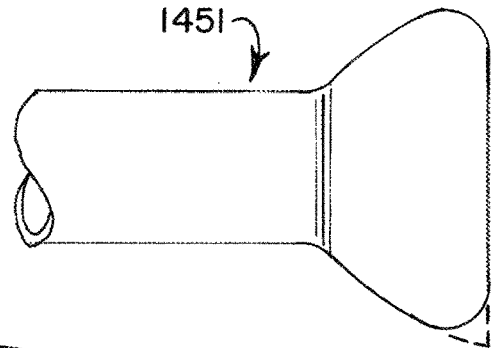
FIG. 12C depicts a side view of the expansile tip of FIG. 12B according to this disclosure.
Figure 12D:
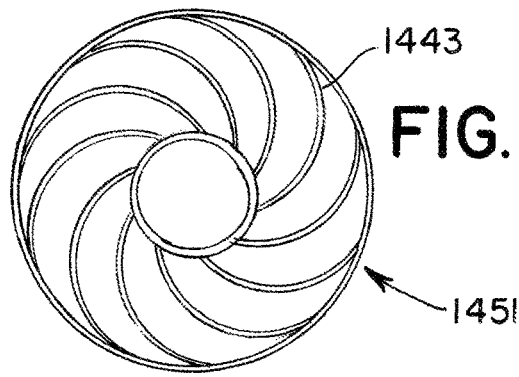
FIG. 12D depicts a front view of the expansile tip of FIG. 12B according to this disclosure.

FIGS. 12B-12D depicts views of tip 1451 once expanded and inverted to the funnel shape, according to this disclosure. In particular, FIG. 12C is a side plane view of tip 1451 with an example coating (though a coating is not necessarily required) whereas FIG. 12D is a front plan view of segment 1451 and FIG. 12B is a rear plan view of segment 1451. As shown in FIG. 12D, segment 1443 and its helical configuration can convert segment 1443 to spiral during inversion. As is also evident in FIG. 12C, along the lower dashed lines depicts the inversion seam of a sharper inversion seam design in comparison to a rounded inversion seam that can interact with the vessel wall during use. FIG. 12B shows segments 1447 and 1445 which form the braid's integrity and provide an inversion hinge at the transition point between segments 1445, 1443. Though not shown, it is contemplated that a coating or membrane as described in this disclosure could be used with tip 1451 as needed or required.

FIG. 13 depicts an example construction of one expansile, invertible tip 1551, which can include a braid with proximal 1547, middle 1545, and distal 1543 segments, whereby the braid of tip 1551 may extend from proximal to distal end. Tip 1551 can provide a more rounded inversion seam that can interact with the vessel wall during use.

FIG. 14A depicts an example construction of one expansile, invertible tip 1651, which can include a braid with proximal 1647, middle 1645, and distal 1643 segments. Segment 1639 is proximal of segment 1647 and portion 1641 represents a transition between each segment. Segment 1647 can be relatively stiff, segment 1645 can be relatively flexible, and segment 1643 can include a helical configuration with respect to its filaments. Middle segment 1645 can in turn be configured to distribute the radial force over a larger region during the inversion step of tip 1651. Middle segment 1645 being relatively flexible at the mid-section can also lower structure inflection forces during inversion especially with the added constraints of a low profile vessel, thus reducing radial force exerted by the structure and potential vessel trauma.

FIGS. 14B-14D depicts views of tip 1651 once expanded and inverted to the funnel shape, according to this disclosure. In particular, FIG. 14C is a side plane view of tip 1651 whereas FIG. 14D is a front plan view of segment 1651 and FIG. 14B is a rear plan view of segment 1651. As shown in FIG. 14D, segment 1543 and its helical configuration can convert segment 1543 to spiral during inversion. As is also evident in FIG. 14C, the inversion seam of the rounded lower corners segment 1645 can interact with the vessel wall during use. FIG. 14B shows segments 1647 and 1645 which form the braid's integrity and provide an inversion hinge at the transition point between segments 1645, 1643. An inversion hinge can be applied by heat setting the filaments to have a larger diameter at the center than the proximal and distal ends to promote inflection, the membrane having sufficient resistance to expansion to hold the enlarged diameter in a substantially tubular shape in line with proximal and distal segments in the collapsed configuration. This can be done with a non-shape memory material by using an oversized braid and reducing the distal and proximal diameters through attachment means to the distal pull ring and proximal catheter body respectively (e.g., reflowing jacket material, adhesive or by a restraining ring). Though not shown, it is contemplated that a coating or membrane as described in this disclosure could be used with tip 1651 as needed or required.

FIGS. 15A-16F depicts views of an expansile, invertible tip 1751 according to this disclosure. In FIG. 15A, tip 1751 can include a braided construction with segments 1755 and 1752. Segment 1752 can include a proximal portion 1751 and a distal portion 1759, each with a braid pattern (e.g., the same pattern or a different pattern). A transition portion 1753 can be positioned between segments 1755 and 1752. In some examples of tip 1751, braid wires can loop around ring 1754 to allow rotation of the braid about ring 1754 during inversion, which can facilitate complete inversion of the distal segment 1752. FIG. 15A is denoted strictly for illustrative purposes sections A, B, C. It is understood that braided wires can loop from A to C to A. However, segment 1751 is not so limited and braided wires can also loop from A to B to A. In other examples, braided wires can loop from A to B to A to C to A. In other examples, braided wires can loop from A to C, as well as any combination of these various braided wire loop configurations. In some examples, at least one braid wire of tip 1751 can be twisted just proximal of ring 1754 to hold ring 1754 in place.

Turning to FIG. 15B, a close-up of tip 1751 is shown in the expanded, inverted funnel-shape configuration. Here, it can be seen that segment 1752 has been inverted and expanded as ring 1754 has been translated proximally, as in previous example distal tips of this disclosure. FIG. 15C is a similar view of FIG. 15B, but with the mandrel and/or dilator removed and leaving tip 1751 alone in the expanded, inverted funnel-shape configuration.

Figure 16E:
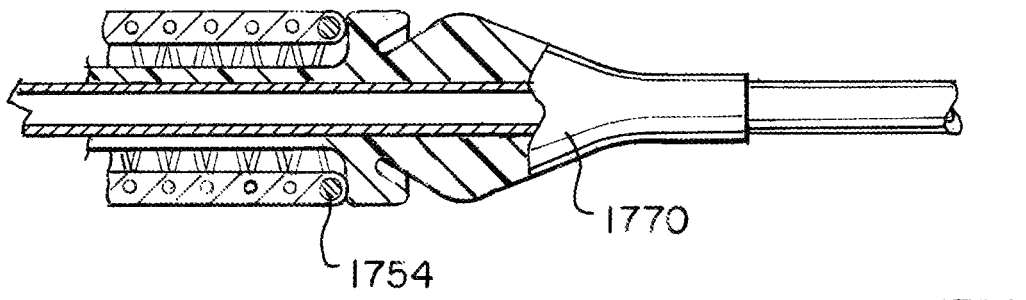
FIG. 16E depicts a close-up view of the expansile tip of FIG. 15A according to this disclosure.
Figure 16F:
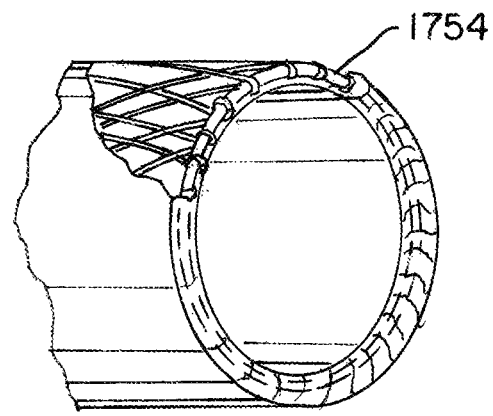
FIG. 16F depicts a close-up view of the expansile tip of FIG. 15A according to this disclosure.

FIG. 16A is a close-up view of section A of FIG. 15A showing braided wires as previously described. FIG. 16B is a close-up view of section B of FIG. 15A showing braided density or PPI change as previously described. FIG. 16C is a close-up view of section C of FIG. 15A showing braided wires looped around pull ring as previously described. FIG. 16D is a close-up cross-section view of section C of FIG. 15A along center line with an example dilator 1770 coupled with ring 1754. As shown, dilator 1770 has circumferential ribs to grip pull ring 1754. FIG. 16E is a close-up cross-section view of section C of FIG. 15A along center line with another example dilator 1770 coupled with ring 1754, whereby dilator 1770 includes abutment features that fold distally to aid radial compression to squeeze through ring 1754 after reaching a predetermined force. FIG. 16F is a close-up perspective view of section C of FIG. 15A showing braided wires looped and coupled with ring 1754, as previously described. The filaments in the present example can extend proximal to distal and can be looped back at the distal end. Ring 1754 can be threaded through the looped ends such that when inverted the looped filaments rotate about ring 1754 to invert the outward face to face radially inwardly and thereby form a distal facing funnel, as shown.

Visibility during deployment of any of the herein disclosed catheter systems can be aided by adding alloying elements (such as palladium, platinum, gold, etc.), by the application of a radiopaque compound, or through the placement of radiopaque markers on one or more of the catheters and devices. Suitable practices are frequently used in connection with other devices and implants and are well known in the art. For example, a radiopaque compound can be incorporated on a cover can be incorporated in the distal tip, or one or more radiopaque markers can be added at, on, and/or adjacent the distal end of the tip. Additionally, one or more of the braid wires may include DFT wire comprising a platinum core (for radiopacity) with NiTi outer layer. With such markers, the physician will be able to visually confirm that the mouth has fully inverted and expanded to the vessel wall.

The aspiration source used in the catheter systems of this disclosure can be a manual syringe or a small-displacement vacuum pump and aspiration directed to the distal tip of any of the herein disclosed catheter systems. Effective aspiration can be accomplished by the sealing action of the inverted, funnel shape of the distal tip with the vessel walls, the interior walls of an outer catheter, and/or through the use of a flow restrictor/seal. In some instances, however, dislodging or fully retrieving a clot with any of the heretofore catheter systems using aspiration alone is not possible. In this respect, it is contemplated that a thrombectomy device can be used with the catheter systems of this disclosure and can be any of a number of commercially available products which can be supplied with or separate from the aspirating clot retrieval catheter. Using a thrombectomy device in conjunction with an expanding mouth catheter system of this disclosure has several benefits to increase the likelihood of first-pass success. The thrombectomy device can support the lumen of the vessel during aspiration such that it will be less likely to collapse under negative pressure, and the thrombectomy device will hold the clot together should the clot comprise an array of stiff and soft portions that may otherwise fragment. The thrombectomy device can also allow the user to pinch a clot that otherwise would not fully enter the lumen of the clot retrieval catheter between the catheter tip and thrombectomy device. A pinched clot will be less likely to dislodge from the clot retrieval catheter as the clot retrieval catheter, clot, and thrombectomy device are retracted as one through the vasculature and outer catheter.

Figure 17:
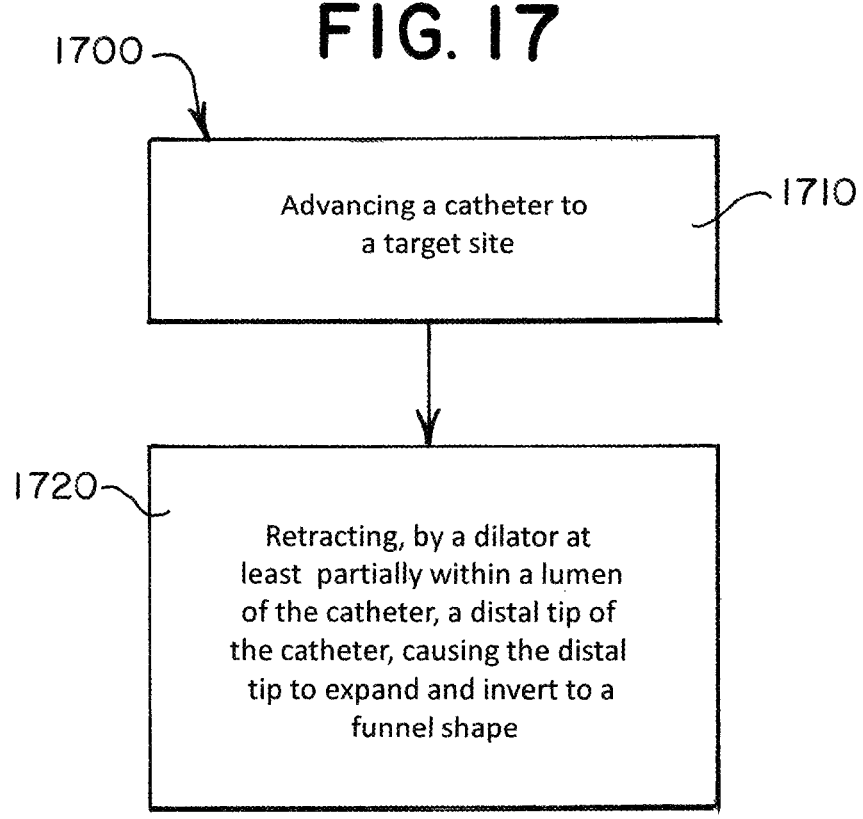
FIG. 17 is a flow diagram outlining a method of use for the system according to aspects of the present disclosure.

FIG. 17 is a flow diagram each comprising method steps for performing a procedure with one system of this disclosure. The method steps can be implemented by any of the example systems, devices, and/or apparatus described herein or by a means that would be known to one of ordinary skill in the art.

Referring the method 1700 outlined in FIG. 17, step 1710 includes advancing any catheter of this disclosure to a target site. Step 1720 includes retracting, by a dilator at least partially within a lumen of the catheter and preferably removing the dilator to maximize aspiration flow rate and force on a clot that is retracted into the catheter, a distal tip of the catheter, causing the distal tip to expand and invert to a funnel shape.

In some examples of method 1700, the dilator can be withdrawn and aspiration can then be applied through the catheter, depending on how the user has deployed the flow restrictions and/or seals, to stimulate the clot into the mouth of the catheter. If aspiration alone is insufficient to dislodge and capture the thrombus or if additional grip on the clot is desired during initial aspiration and dislodgement, a microcatheter with a mechanical thrombectomy clot retrieval device can be advanced to the target. The mechanical thrombectomy device can then be deployed to capture the clot using any method commonly known in the art. Aspiration can continue during the entirety of this step to prevent blood reflux and maintain a tight grip on the clot, or at intervals chosen by the user. In some examples, aspiration and pulling of the clot with a stent retriever may be optimal to increase the chances of first pass success.

In some examples of method 1700, the captured clot and clot retrieval catheter can be withdrawn from the patient or the clot retrieval catheter can be left in place to maintain access as the mechanical thrombectomy clot retrieval device is withdrawn with the clot from the patient. If the clot is observed in the aspiration source and/or thrombectomy device and flow is not blocked in the clot retrieval catheter, this step can also involve carefully injecting contrast under low pressure through the system using known techniques to determine if the vessel is patent. If the vessel is patent, the clot retrieval catheter can be removed. If a blockage remains, additional passes of aspiration, thrombectomy or a combination of these may be repeated until the vessel is patent.

The disclosure is not necessarily limited to the examples described, which can be varied in construction and detail. The terms "distal" and "proximal" are used throughout the preceding description and are meant to refer to a positions and directions relative to a treating physician or user. As such, "distal" or "distally" refer to a position distant to or a direction away from the physician. Similarly, "proximal" or "proximally" refer to a position near to or a direction towards the physician. Furthermore, the singular forms "a", "an", and "the" include plural referents unless the context clearly dictates otherwise.

As used herein, the terms "about" or "approximately" referring to any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the disclosure. It is also to be understood that the mention of one or more steps of a method does not preclude the presence of additional method steps or intervening method steps between those steps expressly identified. Some steps of a method can be performed in a different order than those described herein without departing from the scope of the disclosed technology. Similarly, it is also to be understood that some of the method steps may be omitted.

The mention of one or more components in a device or system does not preclude the presence of additional components or intervening components between those components expressly identified. For clarity and conciseness, not all possible combinations have been listed, and such modifications are often apparent to those of skill in the art and are intended to be within the scope of the claims which follow.

What is claimed is:

1. A catheter system actuatable to a deployed state, comprising:
   a catheter body comprising a lumen; and
   a dilator positioned at least partially within the lumen, a distal end of the dilator releasably connected to a distal tip of the catheter body, the dilator being retractable to expand and invert the distal tip such that the distal tip forms a funnel shape in the deployed state;
   the distal tip comprising:
      a proximal segment; and
      a distal segment extending from the proximal segment, the distal segment being substantially flexible, the distal segment further comprising a proximal end and a distal end, the proximal end comprising a first mating surface;
   a pull ring adjacent to the distal end of the distal segment, the pull ring comprising a second mating surface,
   wherein the first mating surface and the second mating surface are configured to snap lock together.

2. The system of claim 1, wherein a midpoint of the distal segment in a collapsed state transitions to being a distalmost atraumatic end of the funnel shape in the deployed state distal of the catheter body.

3. The system of claim 1, the distal segment in a collapsed state being substantially tubular and in the deployed state comprising the funnel shape, an air cushion formed by the funnel shape between the distal end of the distal segment and the pull ring.

4. The system of claim 1, the distal segment divided into a proximal braid portion and a distal spiral portion.

5. The system of claim 1, the dilator comprising
   a proximal dilator segment;
   a distal dilator segment distal of the proximal dilator segment comprising a diameter greater than a diameter of the proximal dilator segment, the distal dilator segment comprising a contact element extended radially outward from the distal dilator segment and configured to contact and translate proximally the pull ring until the pull ring is aligned at or adjacent to the proximal end of the distal segment extended from the proximal segment of the distal tip.

6. The system of claim 5, the contact element comprising an interference fit with the distal end of the distal tip of the catheter body.

7. The system of claim 5, the distal segment of the dilator comprising a greatest diameter at the contact element and decreases from the contact element to the distal end of the distal segment.

8. The system of claim 5, the distal segment of the dilator comprising a greatest diameter at the contact element and tapers from the contact element to a junction between the proximal segment of the dilator and the distal segment of the dilator.

9. The system of claim 5, the proximal segment of the dilator being highly flexible or substantially more flexible than the distal segment of the dilator.

10. The system of claim 9, further comprising:
    a substantially flexible segment extending distally of the stiffer distal segment, the substantially flexible segment being a short nose.

11. The system of claim 5, the proximal segment of the dilator comprising a fiber reinforcement system to negate elongation.

12. The system of claim 1, wherein the proximal end of the distal tip and the pull ring are locked together in the deployed state.

13. The system of claim 1, the distal tip being configured to first expand to a substantially conical shape before inverting to form the funnel shape.

14. The system of claim 1, the distal tip comprising a braid comprising proximal, middle, and distal portions, wherein the braid comprises filaments extended from the proximal portion to the distal portion in a helical configuration, wherein the distal portion comprises sufficient radial force to push the proximal portion radially outwardly while being configured to accommodate various vessel sizes in an atraumatic manner.

15. A method of inverting an expansile catheter in a blood vessel, comprising:
    advancing the catheter to a target site;
    retracting, by a dilator at least partially within a lumen of the catheter, a pull ring approximate a distal tip of the catheter, causing the distal tip to expand and invert to a funnel shape, the pull ring and a proximal end of the distal tip each comprising mating surfaces configured to snap lock together.

16. The method of claim 15, further comprising:
    restricting, by the funnel shape, flow in the blood vessel.

17. The method of claim 15, further comprising:
    withdrawing the dilator from the catheter;
    aspirating through the catheter to stimulate a thrombus into a mouth of the funnel shape; and withdrawing the catheter with the thrombus from a patient.

18. The method of claim 15, further comprising:
capturing an occlusive thrombus with a mechanical thrombectomy device; and
withdrawing the mechanical thrombectomy device into the funnel shape of the catheter.

\* \* \* \* \*